(12) United States Patent
Dothie et al.

(10) Patent No.: US 8,398,538 B2
(45) Date of Patent: Mar. 19, 2013

(54) SLEEP MANAGEMENT METHOD AND SYSTEM FOR IMPROVING SLEEP BEHAVIOUR OF A HUMAN OR ANIMAL IN THE CARE OF A CARER

(75) Inventors: Pamela Ann Dothie, Oxford (GB); Thomas Alexander Ford, Oxford (GB)

(73) Assignee: Sharp Kabushiki Kaisha, Osaka (JP)

( * ) Notice: Subject to any disclaimer, the term of this patent is extended or adjusted under 35 U.S.C. 154(b) by 100 days.

(21) Appl. No.: 12/837,238

(22) Filed: Jul. 15, 2010

(65) Prior Publication Data

US 2011/0015467 A1    Jan. 20, 2011

(30) Foreign Application Priority Data

Jul. 17, 2009   (GB) .................................. 0912465.2

(51) Int. Cl.
*A61M 21/00* (2006.01)
(52) U.S. Cl. ....................................................... 600/26
(58) Field of Classification Search ................... 600/26, 600/300
See application file for complete search history.

(56) References Cited

U.S. PATENT DOCUMENTS

| | | | |
|---|---|---|---|
| 4,640,034 A | 2/1987 | Zisholtz | |
| 4,777,938 A | 10/1988 | Sirota | |
| 5,479,939 A | 1/1996 | Ogino | |
| 5,813,993 A * | 9/1998 | Kaplan et al. ................. | 600/544 |
| 6,468,234 B1 | 10/2002 | Van der Loos et al. | |
| 6,605,038 B1 | 8/2003 | Teller et al. | |
| 6,648,820 B1 | 11/2003 | Sarel | |
| 7,127,074 B2 | 10/2006 | Landa | |
| 7,689,437 B1 | 3/2010 | Teller et al. | |
| 2002/0019586 A1 | 2/2002 | Teller et al. | |
| 2004/0034289 A1 * | 2/2004 | Teller et al. ................... | 600/300 |
| 2004/0039254 A1 | 2/2004 | Stivoric et al. | |
| 2004/0133081 A1 | 7/2004 | Teller et al. | |
| 2004/0152957 A1 | 8/2004 | Stivoric et al. | |
| 2005/0113650 A1 | 5/2005 | Pacione et al. | |
| 2005/0113703 A1 | 5/2005 | Farringdon et al. | |
| 2005/0143617 A1 | 6/2005 | Auphan | |
| 2005/0245839 A1 | 11/2005 | Stivoric et al. | |
| 2006/0031102 A1 | 2/2006 | Teller et al. | |

(Continued)

FOREIGN PATENT DOCUMENTS

| | | |
|---|---|---|
| EP | 1 810 710 A1 | 7/2007 |
| EP | 2 033 681 A1 | 3/2009 |

(Continued)

OTHER PUBLICATIONS

J. Mindell & J. Owens, "A Clinical Guide to Pediatric Sleep Diagnosis and Management of Sleep Problems", Lippincot Williams & Wilkins, 2003.

(Continued)

*Primary Examiner* — Christine Matthews
(74) *Attorney, Agent, or Firm* — Renner, Otto, Boisselle & Sklar, LLP

(57) ABSTRACT

A sleep management method and system for use by a carer to improve the sleep behavior of a child in their care by monitoring one or more objective parameters relevant to sleep quality and providing one or more recommendations for behavioral programs and/or actions to the carer via a portable user interaction device such as a mobile phone. Such a system can also be adapted for use in looking after adults and animals such as domestic pets.

2 Claims, 12 Drawing Sheets

U.S. PATENT DOCUMENTS

| | | |
|---|---|---|
| 2006/0122474 A1 | 6/2006 | Teller et al. |
| 2006/0224051 A1 | 10/2006 | Teller et al. |
| 2006/0264730 A1 | 11/2006 | Stivoric et al. |
| 2007/0100666 A1 | 5/2007 | Stivoric et al. |
| 2007/0173705 A1 | 7/2007 | Teller et al. |
| 2007/0191692 A1 | 8/2007 | Hsu et al. |
| 2007/0279234 A1 | 12/2007 | Walsh |
| 2008/0161654 A1 | 7/2008 | Teller et al. |
| 2008/0161655 A1 | 7/2008 | Teller et al. |
| 2008/0161707 A1 | 7/2008 | Farringdon et al. |
| 2008/0161715 A1 | 7/2008 | Stivoric et al. |
| 2008/0167535 A1 | 7/2008 | Stivoric et al. |
| 2008/0167536 A1 | 7/2008 | Teller et al. |
| 2008/0167537 A1 | 7/2008 | Teller et al. |
| 2008/0167538 A1 | 7/2008 | Teller et al. |
| 2008/0167539 A1 | 7/2008 | Teller et al. |
| 2008/0167572 A1 | 7/2008 | Stivoric et al. |
| 2008/0167573 A1 | 7/2008 | Stivoric et al. |
| 2008/0171918 A1 | 7/2008 | Teller et al. |
| 2008/0171919 A1 | 7/2008 | Stivoric et al. |
| 2008/0171920 A1 | 7/2008 | Teller et al. |
| 2008/0171921 A1 | 7/2008 | Teller et al. |
| 2008/0171922 A1 | 7/2008 | Teller et al. |
| 2008/0171943 A1 | 7/2008 | Farringdon et al. |
| 2008/0177158 A1 | 7/2008 | Teller et al. |
| 2008/0177193 A1 | 7/2008 | Farringdon et al. |
| 2008/0183051 A1 | 7/2008 | Teller et al. |
| 2008/0183052 A1 | 7/2008 | Teller et al. |
| 2008/0183082 A1 | 7/2008 | Farringdon et al. |
| 2008/0183090 A1 | 7/2008 | Farringdon et al. |
| 2008/0214949 A1 | 9/2008 | Stivoric et al. |
| 2008/0275309 A1 | 11/2008 | Stivoric et al. |
| 2008/0287751 A1 | 11/2008 | Stivoric et al. |
| 2008/0287817 A1 | 11/2008 | Stivoric et al. |
| 2009/0118590 A1 | 5/2009 | Teller et al. |
| 2009/0177068 A1 | 7/2009 | Stivoric et al. |
| 2010/0099954 A1* | 4/2010 | Dickinson et al. ............ 600/300 |
| 2010/0286532 A1 | 11/2010 | Farringdon et al. |

FOREIGN PATENT DOCUMENTS

| | | |
|---|---|---|
| GB | 2 174 225 A | 10/1986 |
| JP | 2004-097495 A | 4/2004 |
| JP | 2004-110486 A | 4/2004 |
| JP | 2004-313461 A | 11/2004 |
| JP | 2004-344265 A | 12/2004 |
| JP | 2007-505412 A | 3/2007 |
| JP | 2007-265379 A | 10/2007 |
| JP | 4035360 B2 | 11/2007 |
| JP | 2008-011865 A | 1/2008 |
| JP | 2009-027638 A | 2/2009 |
| WO | 2005/089649 A1 | 9/2005 |
| WO | 2006/046648 A1 | 5/2006 |
| WO | 2007/143535 A2 | 12/2007 |

OTHER PUBLICATIONS

"Sleep Problems in Children and Adolescents", G. Stores, Oxford University Press, 2009.

Search Report for corresponding European patent application No. 10169738.1 dated Nov. 21, 2012.

* cited by examiner

SLEEP MANAGEMENT METHOD AND SYSTEM FOR IMPROVING SLEEP BEHAVIOUR OF A HUMAN OR ANIMAL IN THE CARE OF A CARER

This nonprovisional application claims priority under 35 U.S.C. §119(a) on Patent Application No. 0912465.2 filed in the United Kingdom on Jul. 17, 2009, the entire contents of which are hereby incorporated by reference.

FIELD OF THE INVENTION

The present invention relates to a system and method for use by a carer for improving the sleep of children. Such a system and method may also be used by a carer in looking after an adult, for example an elderly person, and may also be applied to animals, e.g. domestic pets.

BACKGROUND TO THE INVENTION

Children offer suffer from difficulties going to sleep at bedtime or from wakening during the night and being unable to return to sleep. Studies have shown that 20-50% of infants, toddlers and preschool children experience problems of this sort at some point. If a young child has sleep problems, the whole family is often affected due to disturbance during the night and difficult behaviour during the day. Therefore there is a need to address sleep problems in children.

If childhood sleep problems are not addressed they can persist into later childhood and teenage years. Lack of good quality sleep in children has been linked to a variety of developmental and behavioural problems. Increased sleepiness has been linked to increased oppositional and inattentive behaviour, impaired verbal fluency and creativity, a reduction in the speed and accuracy at which tasks are completed and a decrease in the ability to perform abstract problem solving. A chronic lack of sleep is therefore damaging for a child's academic and social development and hence may disadvantage the child throughout their life. It is therefore clear that addressing childhood sleep problems early is necessary and has great benefits both for the child and for the rest of the family.

As children age, the types of sleep problems they can suffer from change. Newly born babies of up to around 2 months are not able to distinguish night from day and typically sleep for numerous short periods. From 2 months to about 2 years of age, children start to sleep for longer periods and have to learn to adjust their sleep patterns in order to sleep during the night and be active during the day. As the child learns how to sleep it may form maladaptive associations, for example associating the onset of sleep with receiving attention from a parent or carer. The child may then require such attention in order to initiate sleep at bedtime. It is normal for children to arouse 4 to 6 times during the night but if a child has formed an association between going to sleep and receiving attention from a carer, it may cry or wail until the carer comforts it. This causes disrupted sleep both for the parents or carer and for the child. An inappropriate or uncomfortable bedroom environment, that may be too hot or noisy, may also affect the sleep of children of this age.

As children become more independent from about to 2 to 5 years they often start to stall at bedtime, refuse to go to bed or leave their bedroom. This can be because the children seek attention from their parents or carer and may prioritise this over feelings of tiredness. If the parents or carers do not or inconsistently enforce a bed time for the child, older children in particular rapidly learn that they can get away with staying up later if they are difficult at bedtime. This often leads to the children not receiving the duration of sleep they require. These problems can be aggravated further by busy sleeping environments, such as a room shared with another child or sleep-incompatible behaviours such as late-night television watching. Once a child has developed inappropriate sleep habits they can be difficult for a parent or carer to address.

For school age children of 5 years and above, the imposition of a different weekday and weekend schedule can lead to sleeping excessively late during weekend mornings and being unable to readjust to a weekday routine. Furthermore, the presence of a television or video game system in the child's room, if used in the evening, can lead to a delay in the onset of sleep and accompanying problems with daytime sleepiness. If unaddressed these problems can have a deleterious effect on the performance of the child at school and in later life.

Fortunately, many sleep problems in children can be addressed by established behavioural means. By setting and enforcing appropriate sleep times, removing distractions, ensuring a good sleep environment and timing parental contact, the child's quality of sleep can be improved in the majority of cases. Behavioural programs of this nature are typically carried out by a sleep specialist who will work with the parents and child. Since the sleep problems of each child are different, the behavioural programs must be customised to the particular child. The role of the parent or carer is fundamental in teaching the children improved sleep habits but the parent or carer must be educated and trained in how to carry out the behavioural programs. This involves adhering strictly to the program of actions and keeping proper records. Complying with the program of actions can be difficult for the parent or carer, particularly if they do not see improved sleep behaviour in the child immediately. Furthermore, keeping accurate records of the child's sleep may be difficult for the parent or carer, particularly if they are suffering from sleep deprivation as a result of the child's poor sleep behaviour.

The parent or carer is normally trained by the sleep specialist who is also responsible for designing the behavioural program for the particular child, checking that the parents are adhering to the scheme and monitoring the progress of the child. Furthermore, the behavioural programs are often adapted based on the progress of the child which the sleep specialist will estimate from the parent or carer's records. Since keeping accurate records may be difficult for a parent or carer, it is clear that the effectiveness of the behavioural program may be reduced by inaccurate record keeping.

A typical behavioural program for a child with sleep problems may last weeks or months and entail many consultations with a sleep specialist. This can be expensive or unaffordable for the parent or carer and, since sleep problems in children are very common, there may be insufficient sleep specialists in the community to deal with all parents or carers who need advice.

It is clear therefore that there is a need for a device that can assist a parent or carer to monitor the sleep environment and behaviour of a child and to instruct the parent or carer in how to carry out effective behavioural programs to improve the sleep behaviour of a child.

The following references provide additional background information to the invention.

US Patent Documents
U.S. Pat. No. 4,640,034 Zisholtz (3 Feb. 1987)
U.S. Pat. No. 4,777,938 Sirota (18 Oct. 1988)
U.S. Pat. No. 7,127,074 Landa (24 Oct. 2006)
U.S. Pat. 5,479,939 Ogino (2 Jan. 1996)
US Patent Application 20070279234 Walsh (6 Dec. 2007)
US Patent Application 20070191692 Hsu (16 Aug. 2007)

European Patent Documents
1810710 (25 Jul. 2007)
2033681A1 (11 Mar. 2009)
World Patent Documents
WO 2005089649 (29 Sep. 2005)
Others
A Clinical Guide to Pediatric Sleep, J. Mindell & J. Owens (Lippincott Williams & Wilkins, 2003)
Sleep Problems in Children and Adolescents, G. Stores (Oxford University Press, 2009)

There exist a number of devices that are designed to assist children to sleep during the night. U.S. Pat. No. 4,640,034 'Mobile for infants' describes a mobile to be placed above a child's bed or crib. The mobile responds to a child's crying by moving and playing comforting music or sound to distract a child. U.S. Pat. No. 4,777,938 'Babysitter toy for watching and instructing child' describes a toy that is placed close to a child's bed and responds to a child's crying by playing music, reading a fairy story or making some motion so as to coerce the child to sleep. Published European patent application 2033681 describes a toy for a child that may include sensors and emits light or sound to coerce the child to sleep. Published US Patent Application 20070279234 describes a device emitting an automated light or audio cue in order to train a child to sleep at a particular time. Such devices have the disadvantage that they do not address the root cause of sleep problems in children and act only to mitigate sleep disruption. These devices do not make use of the fact that the parent or carer has the most influence over a child's sleep and is therefore the party that can have the most beneficial effect on the child. Therefore they are likely to be ineffective for children who have become accustomed to requiring the presence of their parents to sleep or who are accustomed to not sleeping until late at night.

U.S. Pat. No. 7,127,074 describes a baby monitor device that can assist a parent or carer in training a child to sleep by muting the sound of the child for a fixed period of time so the child's cries can be ignored. This device has the disadvantage that it does not contain a sensing element and is therefore unable to detect if the parent or carer is correctly carrying out the training program or if the training program is effective. Further, it cannot assist the parents in changing the timing of their contact with the child as its sleeping behaviour improves.

WO 2005/089649 (29 Sep. 2005) proposes an implantable medical device that can be implanted in a patient for use in the determination of the patient's sleep quality. The need to implant the device in the patient is however undesirable. The system is directed solely at improving a medical treatment, for example for chronic pain, and does not teach any system for use by a carer to assist with merely modifying sleep patterns of an individual in their care by any behavioural program.

EP 1810710 (25 Jul. 2007) proposes a sleeping state improvement system for improving the sleeping state of a user who is away from home. It has a memory unit carried by a user, a specification unit and a control unit. The specification unit specifies individual attributes of the user based on individual information, and the individual information is stored in the memory unit. The control unit controls an environment when the user is asleep based on the individual attribute information.

US 2007/0191692 (16 Aug. 2007) relates to a system for monitoring the quality of sleep of a person. The system comprises a sensor for sensing physiological signals such as snoring, breathing, body movement or body temperature. These signals are transmitted from the sensor to a data server via a wired or wireless connection. The signals are stored and analysed by the data server to determine when the person under test is awake or asleep, in deep or shallow sleep, duration of sleep etc.

Whilst there exists a number of devices which attempt to mitigate sleep problems in children, there remains a need for a device that can assist a parent or carer to monitor the sleep behaviour of a child and to instruct the parent or carer in how to carry out effective behavioural programs to improve the sleep behaviour of a child.

SUMMARY OF THE INVENTION

According to a first aspect of the invention, there is provided a method for use by a carer to improve the sleep behaviour of a human or animal in their care, the method comprising: (i) monitoring, using at least one sensor, one or more objective parameters relevant to sleep-related behaviour of said human or animal, said parameters being selected from physiological parameters and environmental parameters and including at least movement of the human or animal and/or electrical signals indicative of brain activity of the human or animal after having been put to bed; (ii) communicating data from said at least one sensor to a processing means; (iii) at said processing means, using said data in selecting from a first memory one or more recommendations for behavioural programs to improve the sleep behaviour of the human or animal and/or actions for implementation by the carer to improve the sleep behaviour of the human or animal; and (iv) sending said one or more recommendations from said processing means to a portable user interaction device for presenting the recommendation(s) to the carer via a display, said portable user interaction device also enabling the carer to input information which is fed back to said processing means; wherein said processing means updates the one or more recommendations sent to said portable user interaction device on the basis of changes in detected sleep behaviour of said human or animal and/or on the basis of information input to said portable user interaction device.

According to another aspect of the invention, there is provided a sleep management system for use by a carer to improve the sleep behaviour of a human or animal in their care, comprising: (i) at least one sensor for monitoring one or more objective parameters relevant to sleep-related behaviour of said human or animal, said parameters being selected from physiological parameters and environmental parameters and including at least movement of the human or animal and/or electrical signals indicative of brain activity of the human or animal after having been put to bed;
(ii) a sensor unit which collects data from said at least one sensor and communicates data to a processing means; (iii) said processing means which uses data from said sensor unit in selecting from a first memory one or more recommendations for behavioural programs to improve the sleep behaviour of the human or animal and/or actions for implementation by the carer to improve the sleep behaviour of the human or animal and (iv) a portable user interaction device, e.g. a mobile phone, which receives said one or more recommendations from said processing means and presents the one or more recommendation(s) to the carer via a display, said portable user interaction device also enabling the carer to input information, for example, on implementation of the recommendation(s) which is fed back to said processing means; said processing means updating the recommendation(s) sent to said portable user interaction device on the basis of changes in detected sleep behaviour of said human or animal and/or on the basis of information input by said carer to said portable user interaction device.

According to another aspect of the invention, there is provided a method of improving the sleep behaviour of a human or animal, the method comprising:
(i) receiving, at a processing means, data from at least one sensor, the data relating to one or more objective parameters relevant to sleep-related behaviour of said human or animal, said parameters being selected from physiological parameters and environmental parameters and including at least movement of the human or animal and/or electrical signals indicative of brain activity of the human or animal after having been put to bed; (ii) at said processing means, using said data in selecting from a first memory one or more recommendations for behavioural programs and/or actions for implementation by the carer and (iii) sending said one or more recommendations from said processing means to a portable user interaction device for presenting the recommendation(s) to the carer via a display; wherein said processing means updates the one or more recommendations sent to said portable user interaction on the basis of changes in detected sleep behaviour of said human or animal and/or on the basis of user information received from said portable user interaction device.

The invention will be described in more detail below with reference to the figures and with particular reference to modifying sleep of a child.

DETAILED DESCRIPTION OF PREFERRED EMBODIMENTS

A system is thus provided to assist a parent or another carer to monitor the sleep behaviour of a child and to instruct the parent or other carer in how to carry out effective behavioural programs to improve the sleep behaviour of a child. The system may further personalise the behavioural program to the particular child. The system tracks any improvement in sleep behaviour of the child and adapts the behavioural program based on improvement. The system assesses the compliance of the parent or carer to the program and provides such encouragement and guidance as may be necessary. The system can be used without external advice and provides a complete system for improving a child's sleep. Alternatively it can be used as an aid for a parent or carer who is receiving advice from a sleep specialist.

The system may comprise a sensor unit to be placed close to the sleeping child, a portable device for the use of a parent or carer and a processing unit. As indicated above, the processing unit may be disposed in a separate device or in one of the sensor unit or the portable unit. As an alternative to a hardware unit, the required processing means may preferably take the form of a software service accessible via a wide-area network, preferably the Internet.

Figure 1:
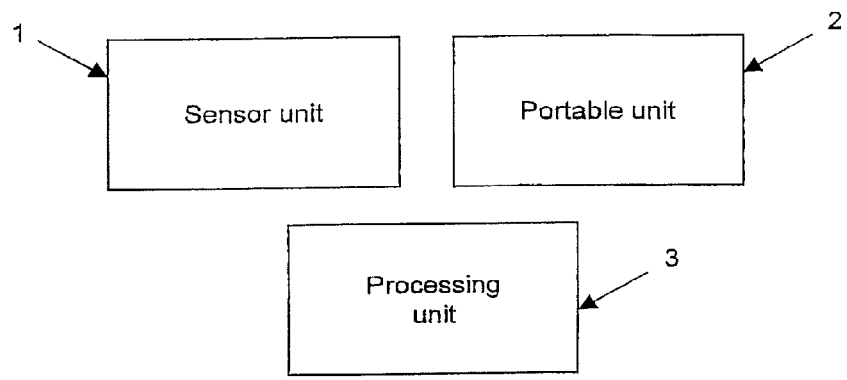
FIG. 1 shows the main components of the system: sensor unit (1), handheld unit (2) and processing means shown as a separate processing unit (3).

As indicated above, the sensors may be integral to the sensor unit as shown in FIG. 1, but it may be preferred for at least one sensor, e.g. a movement sensor such as a sensor comprising a piezoelectric element, to be external to the sensor unit and connected thereto either by a cable or a wireless connection. Environmental parameters monitored may include one or more of temperature, ambient noise and light, preferably all of those parameters. Humidity may also be monitored. In some instances, pressure monitoring may be provided. The sensor unit records physiological data about the child when in its bed or crib. The sensor unit also preferably records environmental data about the sleeping area.

Figure 2:
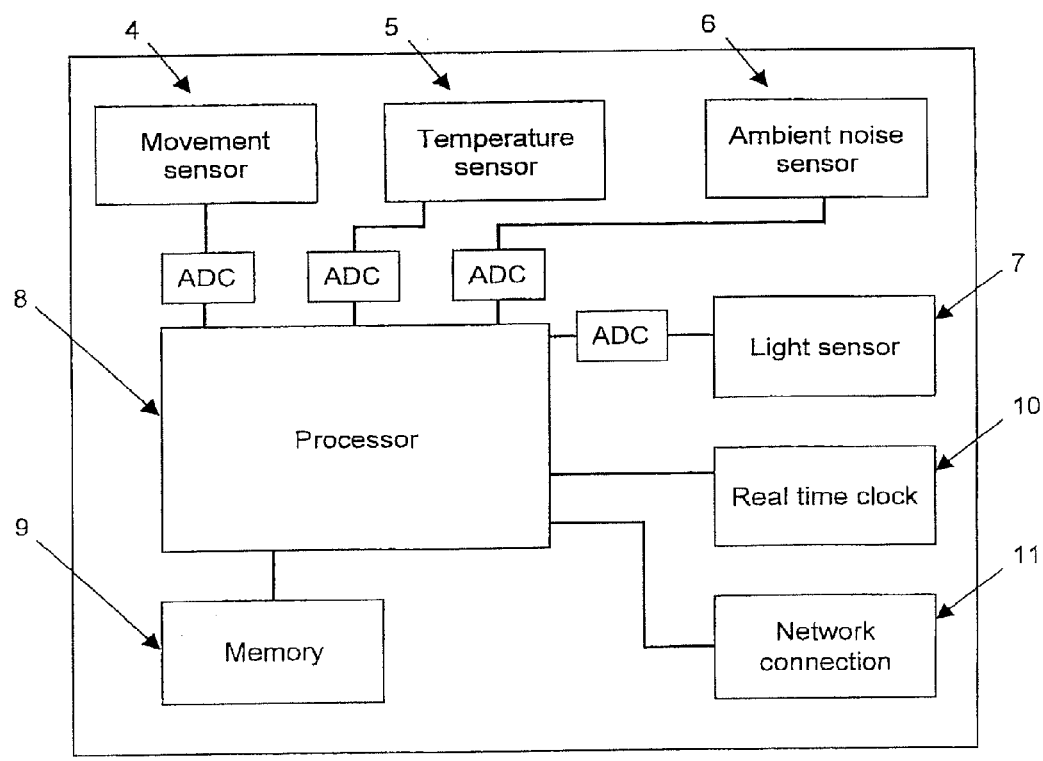
FIG. 2 is a schematic diagram of one embodiment of a sensor unit suitable for use in the invention.
Figure 4:
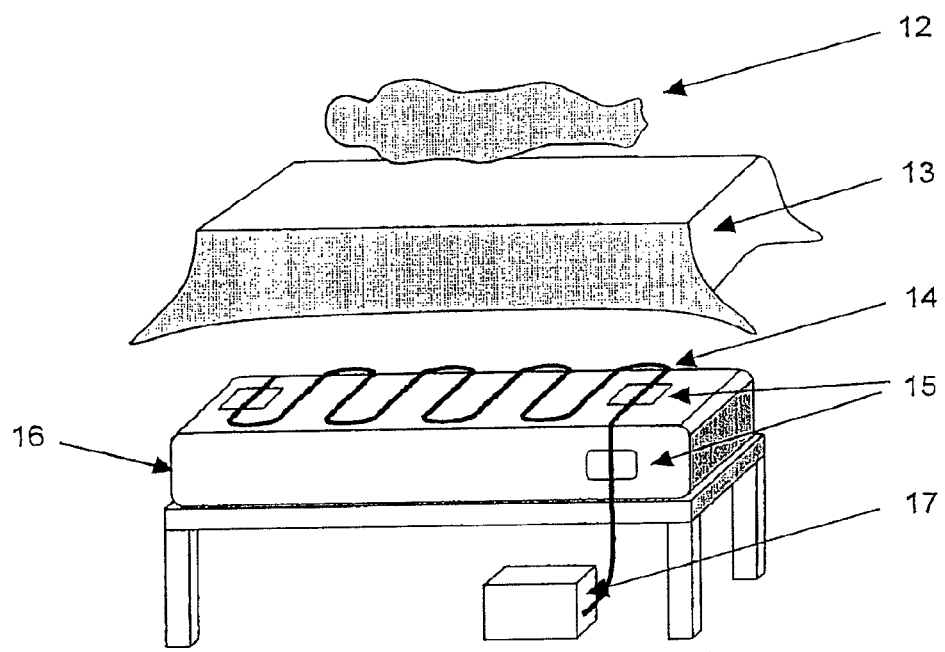
FIG. 4 is a schematic illustration of a bed suitable for use in a system of the invention.
Figure 7:
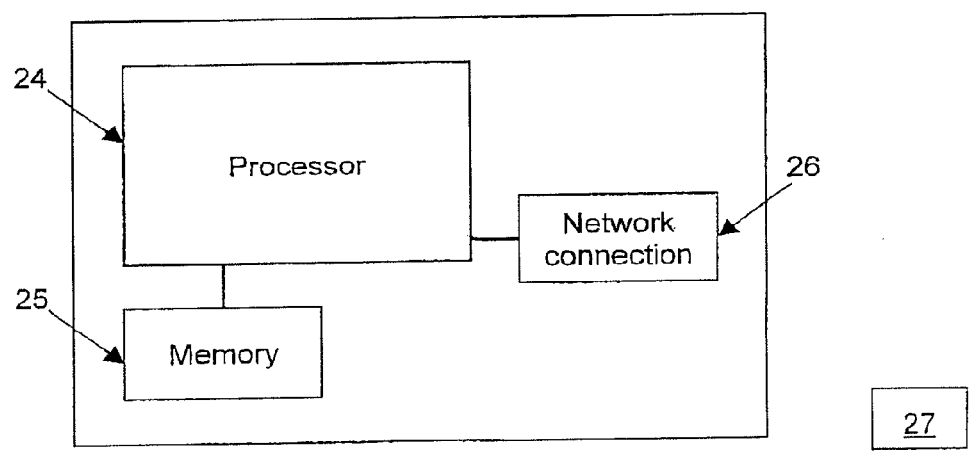
FIG. 7 is a schematic diagram of a processing unit equating with the required processing means of a system of the invention.

FIG. 2 shows one sensor unit suitable for use in the invention. The sensor unit of FIG. 2 collects data from a plurality of sensors, a movement sensor, a temperature sensor, an ambient noise sensor and a light sensor (4, 5, 6, 7) and provides data from each sensor to a processor (8) via a plurality of analogue-to-digital converters (ADCs). Processed sensor data is stored in a memory (9) of the sensor unit with a time code provided by the real time clock (10) and sent to an external processing means, e.g. a processing unit as shown in FIGS. 1 and 7, via the network connection (11). The sensors are shown as integral to the sensor unit, but one or more sensors may alternatively be external to the sensor unit and connected to the sensor unit via a cable or wireless connection. For example, the movement sensor may comprise a piezoelectric element on a bed and connected to the sensor unit by a cable as shown in FIG. 4.

The physiological data and environmental data is collected and sent to the processing means (3). The sensor unit may preferably contain a real time clock (10) whereby each sensor reading, or multiple of sensor readings from each sensor for storing in the memory (9) of the sensor unit, is stored with a time code. Such stored data may be sent periodically, or on request, to the processing means (3).

The parent or other carer interacts with the system via a portable device. The device allows the carer to monitor the sleep patterns and preferably also the sleeping environment of the child. It further educates the carer as to effective means of altering (alerting means) the behaviour of the child, allows the carer to choose a suitable behavioural program, assists the carer in carrying out the program and provides encouragement and collects feedback. Choices selected by the carer on the portable device are sent to the processing means (3). The portable unit desirably features a means of alerting the carer as to when to carry out some action with the child during the course of a behavioural program. FIG. 7 shows one example of a processing means (3) suitable for use in the invention, having a processor (24), and memory (25) and a network connection (26).

The processing means (3) collects sensor data from the sensor unit (1) and stores them in a memory, for example in its memory (25). It analyses the sensor data to extract one or more metrics which are used to monitor the child's sleep patterns and behaviour during the period in bed. It also desirably analyses sensor data about the child's sleeping environment to ensure it is not adversely affecting the child's sleep. The processing unit makes these sleep metrics and the original data available to the carer via the portable unit (2) as required. As is known, a "sleep metric" is a standard measurement used to describe or characterise sleep and includes information relating to sleep such as, for example, one or more of: total sleep time, time in bed, sleep onset latency, total wake after sleep onset, number of awakenings after sleep onset, etc. A sleep metric is usually expressed as a number, and possibly as a number expressed relative to another number (for example as a percentage). The invention may additionally or alternatively use a "sleep quality metric", which is a measurement which can be used to describe the quality of sleep, such as, for example, sleep efficiency (the proportion of time in bed that is spent sleeping, significant movement (a sleep quality metric based on the number of significant movements a person makes whilst asleep), sleep fragmentation (a metric based on based on the number of awakenings after sleep onset) etc. Primarily, the movement data is analysed to calculate these sleep metrics, but the other sensor data, especially light and noise, can also be used along with the movement data in order to calculate these sleep metrics.

The processing means (3) also uses the sleep metrics to characterise the child's current sleep behaviour and to select appropriate behavioural programs for the child. The metrics are further used to customize the parameters of any behavioural program so as to be suitable for the particular child. When the carer is carrying out a chosen behavioural program, the metrics are checked to ensure that the carer is carrying out the program correctly, ensuring compliance. During the course of the program the metrics are used to judge any improvement or worsening of the child's sleep behaviour and the parameters of the behavioural program are changed in response to this. If a behavioural program is not in progress the metrics are checked for any unusual changes in the child's sleep behaviour in which case the carer will be informed and a suitable behavioural program recommended.

The processing means (3) also records the interactions by the parent or other carer with the portable unit in a memory, for example in its memory (25). The record of these interactions and the sensor data metrics are checked to ensure that the carer is carrying out any behavioural program correctly. To aid compliance, and especially if the carer is not carrying out a behavioural program correctly, then the processing unit may provide warnings and/or guidance and/or advice and/or message(s) of encouragement via the portable unit. It may alternatively or additionally provide one or more updated recommendations for behavioural programs and/or actions if lack of compliance or lack of effectiveness is detected. For example, the processing means may provide an alert via the portable device, which may be one or more of an audio or vibration signal or message via the display, after a pre-defined number of nights of lack of improvement in sleep behaviour or after a pre-defined number of nights of worsening of sleep behaviour. Furthermore, the processing means may respond to any request sent by the parent or other carer via the portable unit for further information and guidance at any time.

Prior to recommendation of any behavioural program or action to be applied to a particular child, the sensor unit will preferably send data to the processing means (3) for a period whereby a baseline for each sensor signal and/or a baseline sleep metric is established. Further information on one implementation of a system of the invention is provided in the exemplification below.

From the above, it will be evident that the following advantages are gained by use of a sleep management system as now taught. Firstly, the system has the advantage of using sensors to assist a parent or other carer to provide an accurate record of the sleep patterns of a child. This record can be used by the carer or given to a sleep specialist or clinician to examine. Since the record is based on sensor data it is more accurate than a record made by the carer by hand.

The system can provide the further advantage of using sensors to record the sleep environment of a child. The sensor data is processed so as to highlight occurrences of interest during the night. This information can be used by a carer to determine if the child's sleep is being disturbed and also if the child is engaged in any distracting activities when they are meant to be sleeping.

The system also has the advantage of selecting appropriate behavioural programs for a child based on the child's sleep behaviour as measured by the sensors. Since several behavioural programs may be appropriate for a child, the system has the advantage of allowing the parent or other carer to select a behavioural program of their choice. Some carers find particular behavioural programs difficult to carry out and are therefore more likely to effectively carry out a program that they have selected.

The system has the further advantage of assisting the carer to carry out a chosen behavioural program on a child to improve the child's sleep behaviour. This may be achieved by alerting the carer at appropriate times and instructing them each night as to which actions to carry out and for how long in order to improve the child's sleep.

Whilst a behavioural program is in progress, the system has the advantage of adapting the behavioural program depending upon the progress of the child, as measured by the sensors. It also has the advantage of ensuring that the program is being carried out correctly by the carer by analysing sensor data and the carer's interactions with the system.

When a program is not being carried out the system has the advantage of detecting any changes in the child's sleeping behaviour and alerting the carer. This allows the carer to intervene before the sleep problems become more serious.

The system has the advantage of being appropriate for children from as young as 2 months up to school-aged children or adolescents. Various behavioural therapies are provided which are suitable for sleep problems that typically occur in different ages of children. The sleep and environment monitoring capability of the system is appropriate for any age of child.

In some embodiments, a system is used by a carer such as a parent to improve the sleep behaviour of a baby, infant or child.

In some embodiments, a system is used by a carer in looking after an adult in their care due to old age or mental or physical disability.

In some embodiments, a system is used by a pet owner in looking after a pet animal in their care.

In some embodiments, a combination of hardware units for implementing a sleep management system is shown, comprising (i) the required sensor(s), (ii) the sensor unit (1) and (iii) the portable user interaction device (2).

In some embodiments, a combination of hardware units is shown wherein the portable user interaction device is a mobile phone.

In some embodiments, a method is applied to improve the sleep behaviour of a baby, infant or child.

In some embodiments, a method is applied to an adult in the care of the carer due to old age or mental or physical disability.

In some embodiments, a method is applied by a pet owner to a pet animal in their care.

In some embodiments, a method is shown wherein the carer inputs information to the portable user interaction device on choice and implementation of a recommended behavioural program or action which is sent to the processing means for correlation with sensor-derived data.

In some embodiments, a method is shown wherein prior to recommendation of any behavioural program or action the sensor unit sends data to the processing means for a period whereby a baseline for each sensor signal and/or a baseline sleep metric is established.

In some embodiments, a method is shown wherein prior to use in improving sleep behaviour of said human or animal, the sensor unit sends data to the processing means for a period whereby a baseline for each sensor signal and for a baseline sleep metric is established.

The following exemplification sets out specific embodiments of the invention by way of example only. Embodiment 3 is provided by way of illustration of extension of the invention to use in improving sleep of non-human animals.

Figure 14:
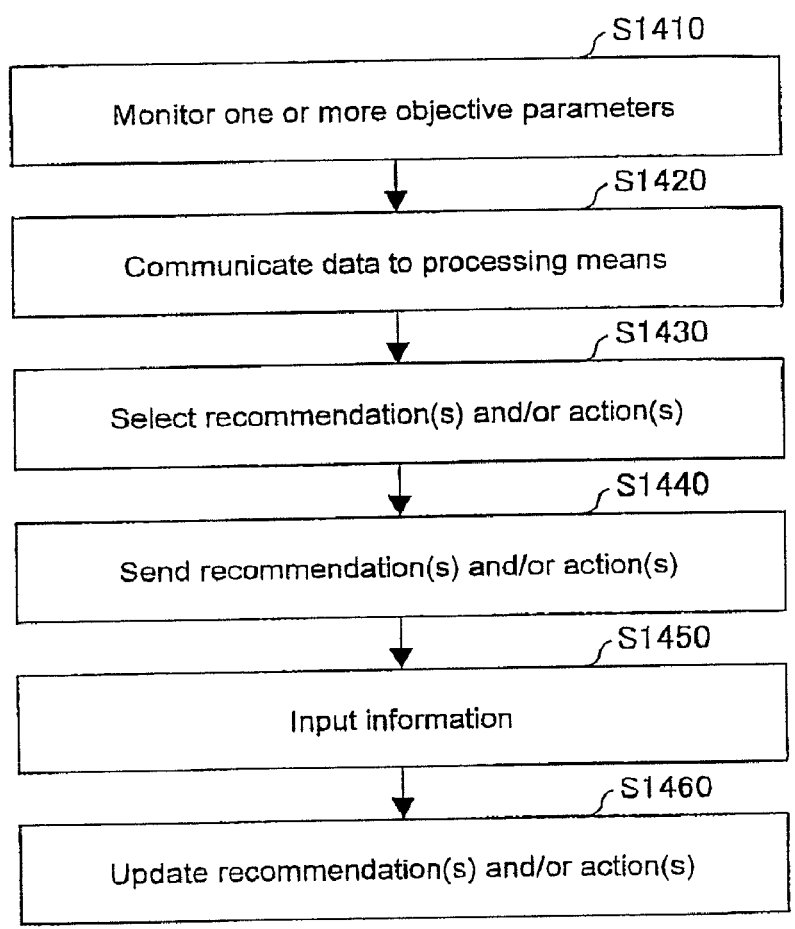
FIG. 14 is a block flow diagram illustrating principal steps of a method according to one embodiment of the invention.

FIG. 14 is a block flow diagram illustrating principal steps of a method of managing the sleep of a human or animal according to one embodiment of the invention. Initially, the method comprises monitoring S1410, using at least one sensor (for example one or more of sensors 4-7 described below with reference to FIG. 1), one or more objective parameters relevant to sleep-related behaviour of the human or animal. The parameter(s) is/are selected from physiological parameters and environmental parameters and include at least movement of the user and/or electrical signals indicative of brain activity of the user.

Preferably the method comprises monitoring both physiological and environmental parameters non-obtrusively such that they do not affect the sleep of the user.

Next, the method comprises communicating S1420 the data from the at least one sensor to a processing means for example the processing means described below with reference to FIG. 7.

Next, the method comprises, at said processing means, using the data from the at least one sensor in selecting S1430 from a first memory one or more recommendations for behavioural programs to improve the sleep behaviour of the human or animal and/or actions for implementation by the carer to improve the sleep behaviour of the human or animal.

Next, the method comprises sending S1440 said one or more recommendations from said processing means to a portable user interaction device, for example a portable user interaction device as described with reference to FIG. 6, for presenting the recommendation(s) to the carer via a display.

The portable user interaction device also enables the carer to input S1450 information, which is fed back to the processing means.

Next, the processing means updates S1460 the one or more recommendations sent to said portable user interaction on the basis of changes in detected sleep behaviour of said human or animal and/or on the basis of information input to said portable user interaction device. These updated recommendations are then displayed to the user on the said portable user interaction device.

EXAMPLES

Embodiment 1

In a first embodiment, the system comprises a sensor unit (1), a portable unit (2) and a processing unit (3). The sensor unit comprises a plurality of sensors (4, 5, 6, 7), hardware and/or software to carry out such data processing as may be necessary (8) and a network connection (11) so as to send data to and receive data from the processing unit. The portable unit comprises a means of communicating information to the parent or other carer (18), a means of recording input from the carer (19) and a network connection (20) so as to send data to and receive data from the processing unit. The processing unit comprises hardware and/or software (24) to analyse data from the sensor unit and portable unit. The processing unit may be disposed in either the sensor unit or the portable unit or may be disposed in a separate device. The processing unit contains a network connection (26) such as to communicate with the sensor unit and portable unit.

FIG. 2 illustrates the components of the sensor unit. The sensor unit includes a plurality of sensors (4, 5, 6, 7). Some sensors monitor the sleeping environment of the child. These include temperature (5), light (7) and ambient noise (6) sensors. Other possible environmental sensors include humidity and pressure sensors.

The sensor unit also includes sensors to monitor physiological parameters of the child whilst in a bed or another sleeping area. These sensors include one or more movement sensors, e.g. an infra-red sensor or other movement sensor (4), to detect the movement of the child when in bed and a noise sensor (6) to detect noises made by the child such as crying. The movement sensor(s) may be sufficiently sensitive to record the breathing and heartbeat of the child, e.g. a sensitive sensor comprising a piezoelectric element. Thus, a movement sensor may be preferably connected to the sensor unit comprising a piezoelectric element as illustrated by FIG. 4 and described in U.S. Pat. No. 5,479,939. Multiple movement sensors may be used so as to measure movement at multiple points on the child's bed or for monitoring more than one child simultaneously. The physiological sensors are preferably non-invasive such that they do not disturb the sleep of the child. The physiological sensors are used to record information about the child's behaviour in bed whilst awake or asleep. The absence of data from the physiological sensors can be used to indicate that the child is not present in the bed.

The sensors are in general implemented with a sensing element, amplification and filtering elements and an analogue-to-digital converter (ADC) to create a digital signal that can be analysed by a processor. Signal data may desirably be sampled by the processor (8) of the sensor unit at low frequency before storage to memory as further discussed below.

Possible sensing elements for temperature include a thermistor, thermocouple or similar device. Possible sensing elements for light include a photodiode or photoresistor. Logarithmic amplification may be used for the light, movement or noise sensors to increase dynamic range.

Figure 3:
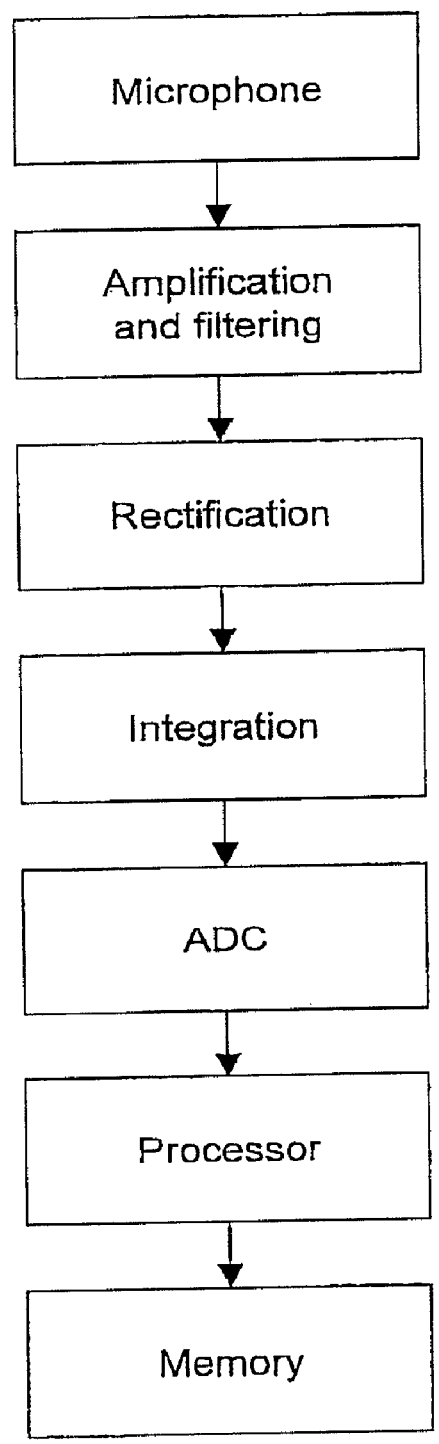
FIG. 3 is a schematic diagram of an ambient noise sensor.

FIG. 3 shows an implementation of an ambient noise sensor that can detect environmental noise or crying or other noises produced by the child. Recording the ambient noise for an entire night at the typical sampling rate and precision of a CD or similar audio recording device requires a large amount of storage memory and a large amount of CPU time to process said data. Therefore the ambient noise sensor is designed to produce a slowly-varying signal that is characteristic of the loudness of the ambient noise that has occurred in the last few seconds. This signal then can be sampled at a much lower frequency (between 0.1 Hz and 100 Hz) than the unprocessed audio signal and therefore requires very much less storage in the sensor unit and processing capability in the processing unit (3).

A compact microphone detects ambient noise and produces a small AC voltage signal. This is then amplified and filtered by circuitry, which passes audio frequencies only (typically between 100 Hz and 20 kHz). The amplified AC signal is rectified by circuitry. The rectified AC signal is then integrated by circuitry. The integrator has a time constant of several seconds. In this way the AC signal representing a sound of duration less than a second becomes a DC signal that persists for several seconds. This DC signal is converted into a digital signal by the ADC. The processor (8) within the sensor unit then records the output of the ADC into a memory (9). Because the DC signal persists for several seconds, the processor (8) can sample at a low frequency (between 0.1 Hz and 100 Hz) and will not miss any sounds that occur between sampling periods. Other implementations of an ambient noise sensor could be used in the system.

FIG. 4 shows the components and deployment of a sensor which records movement of the child when in bed. Sensor (14) is a piezoelectric cable (a movement sensor cable) or film which is placed on the child's bed (17) beneath the sheets (13) upon which the child (12) lies. Attachments (15) keep the cable or film in place and may have clips, buttons, pieces of velcro or similar devices to attach the cable or film to sheets or the mattress (16). Alternatively, the film or cable may be embedded in a complete sheet which is placed under the other bedding sheets. The film or cable is connected to the sensor unit (1) by a cable, e.g. an extension of the sensing cable (14). Optionally, the film, sheet or cable comprising a piezoelectric element may instead connect to an interface unit positioned in the bed which is wirelessly connected to the main sensor unit.

Figure 5:
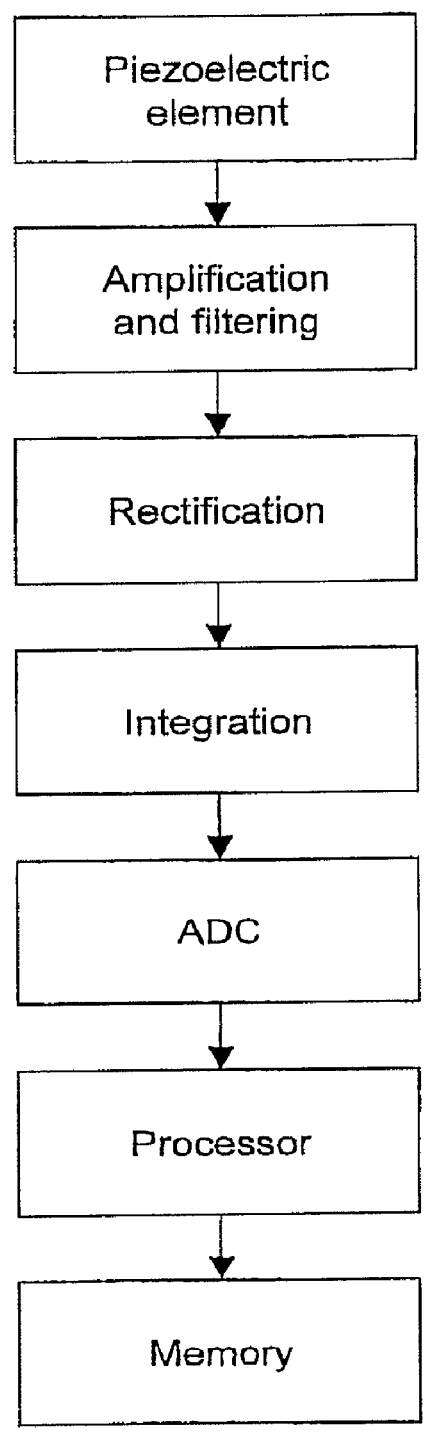
FIG. 5 is a schematic diagram of a movement sensor comprising a piezoelectric element.

FIG. 5 shows an implementation of the system required to process the electrical signal from the piezoelectric film or cable in order to produce a slowly-varying signal that can be sampled at a low frequency (between 0.1 Hz and 100 Hz). For the same reasons as for the ambient noise sensor, sampling at a slow rate produces an advantageously small amount of data to be stored in the memory of the sensor unit.

The piezoelectric film or cable produces a small electrical charge when it is compressed due to a movement of the child's body. The child's body may move due to a gross physical movement (such as moving an arm or leg) or smaller movements due to the process of breathing or the beating of the heart. The small electrical charge caused by a movement appears as a small AC voltage signal across the capacitance of the cable. This AC voltage signal is then amplified and filtered by circuitry which passes low frequencies characteristic of movement, breathing and heart rate only (typically above 0.1 Hz and below 3 Hz). The amplified AC signal is rectified by circuitry. The rectified AC signal is then integrated by circuitry. The integrator has a time constant of several seconds. In this way the AC signal representing a short movement becomes a DC signal that persists for several seconds. This DC signal is changed into a digital signal by the ADC. The processor (8) within the sensor unit then records the output of the ADC into a memory (9).

In addition, the system may sample the AC voltage signal after amplification at a higher frequency (up to 100 Hz) in order to record the small movements due to the breathing and beating of the heart of the child. These data can also be analysed by the processing unit (3) and used to calculate sleep metrics, as explained below.

Other implementations of a movement sensor are possible that provide similar data which can be analysed by the processing unit (3). Table 1 lists different means of sensing the child's movement in bed. Use of a piezoelectric cable, film or sheet is the preferred method since it is non-invasive, easily deployed by a carer and cheap to manufacture.

TABLE 1

Methods for detecting movement of a child during sleep

| | |
|---|---|
| Actigraphy | Actigraph (accelerometer) worn on the child's body |
| Camera | Machine vision techniques used to detect child's movement |
| Capacitive | Capacitive cable, film or sheet placed on child's bed |
| Infrared (IR) | Infrared motion detector |
| Radio frequency (RF) | RF motion detector |
| Piezoelectric | Piezoelectric cable, film or sheet placed on child's bed |
| Ultrasonics | Ultrasonic motion detector |

The movement data of the child is analysed by the processing means (3) in order to calculate sleep metrics, The analysis may include monitoring changes in heart rate, breathing rate and the incidence and frequency of physical movements, The sleep metrics calculated include those shown in Table 2 and relate to finding times and durations of periods of sleep, times and durations of periods spent in bed and sleep quality.

TABLE 2

General sleep metrics

Number, time and duration of nocturnal awakenings
Sleep efficiency (amount of time in bed spent asleep)
Sleep onset latency (time between in bed and first sleep period)
Sleep quality metrics
Time and duration of different sleep stages (I-IV and REM)
Time and duration of events where bed was left
Time of sleep onset events
Time out of bed
Time to bed
Total sleep time
Wake time after sleep onset (total time awake after sleep onset)

It is possible to measure other physiological parameters instead of or in addition to movement which can also be used to analyse the child's sleep and to calculate sleep metrics. The most comprehensive form of sleep analysis is polysomnography (PSG) which includes measurement of brain waves, heart rate, breathing rate, muscle tension and other physiological parameters. Techniques to monitor these physiological parameters include electroencephalography (EEG), electromyography (EMG), electrocardiography (ECG), body straps and nose cannulas. However, since these methods are invasive and require attaching electrodes (which may be disposed in a headband or other worn article) or other devices to the child's body and may disturb the child during the night they are less preferred.

Referring to the schematic of the sensor unit (FIG. 2), the processor (8) in the sensor unit repeatedly samples the sensors at a low frequency (between 0.1 Hz and 100 Hz). The sensor unit contains a real-time clock (10) which provides a time code for each sensor data reading. Each sensor reading along with the time code is stored in the memory (9). A time code may be stored for every sensor reading or for every multiple of sensor readings, for example every 100 readings. The sensor data stored in the memory (9) is sent periodically, or on request, to the processing unit (3) via the network connection (11). It may be desirable to do further processing on the data before sending it to the processing unit (3) since the amount of data recorded may be large. The processor (8) of the sensor unit may therefore compress the data before sending, or analyse the data to extract sleep metrics and send the sleep metrics to the processing unit (3) instead of sending the full data set. The sensor unit may be powered by a direct mains connection or battery. Other implementations of the sensor unit are also possible.

Figure 6:
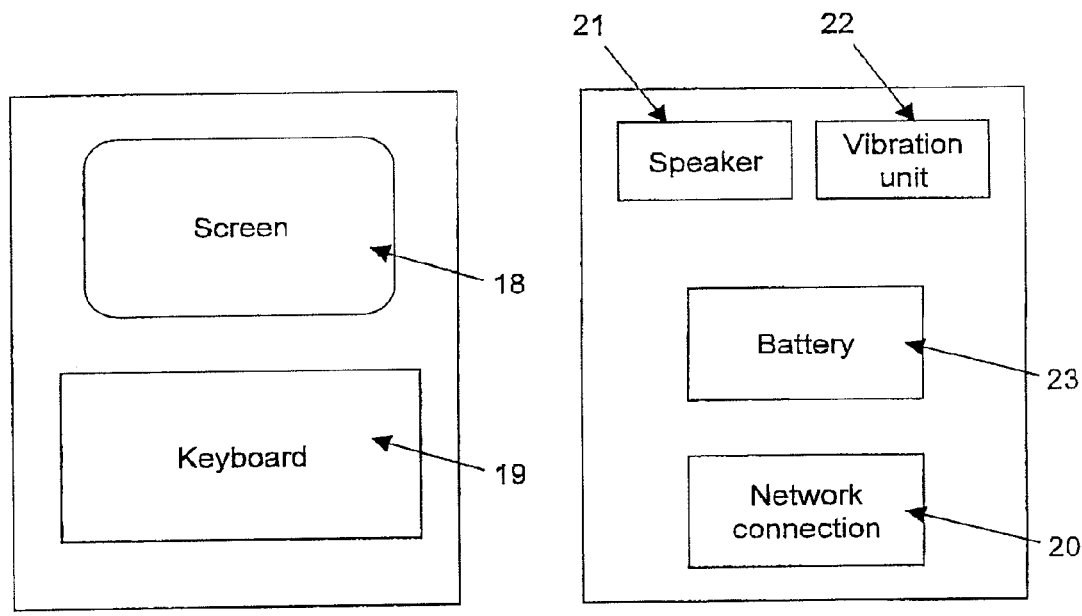
FIG. 6 is a schematic diagram of a portable device for use in a system of the invention with a display screen (18) and keyboard for user input of information (19).

FIG. 6 shows a schematic of the portable unit. The portable unit allows the carer to interact with the system via a display (18) and an input device such as a keyboard (19), mouse, touch screen, gesture camera, microphone or similar device. The portable unit communicates with the processing unit (3) to retrieve information to present to the carer and sends data on user choices and actions using the network connection (20). The portable unit also contains a speaker (21) and a vibration unit (22) which are used to alert or prompt the carer. A battery (23) or similar power system powers the portable unit so it may be carried easily without requiring a wire to a power socket. Other implementations of the portable unit, including those with additional functions, are also possible providing they are sufficient to permit the user to interact with the system as described herein.

The portable unit may be implemented as a custom piece of hardware with dedicated software. In this case, the portable unit may take the form of an alarm clock, a hand-held baby monitor or other suitable item, including the extra functionality of those devices. Furthermore, the portable unit may be dockable with the sensor unit to charge the portable unit or to exchange data between the portable unit and the sensor unit or vice-versa.

It is also possible to implement the functions of the portable unit on a general-purpose device such as a laptop PC, PDA or cell phone. In this case, the functionality of the portable unit described herein is provided in the software. The software makes use of the in-built speaker, vibration unit or other alerting system that is present in the general purpose device. The software also makes use of the network connection of the general purpose device.

FIG. 7 shows the processing unit (3). The processing unit comprises a processor (24), a memory (25) and a network connection (26). The processing unit stores sensor data taken from the sensor unit (1) and usage and user input from the portable unit (2) in the memory (25). The processor analyses the sensor data and calculates a number of sleep metrics which provide useful information about the sleep of the child. Some important metrics calculated by the processing unit are shown in Table 2. These calculated metrics are then stored in the memory (25). The processing unit uses these metrics to select suitable behavioural programs for the child, to personalise the parameters of these programs to the child, to check the compliance of the carer to a program, to measure the efficacy of a behavioural program and to modify the parameters of the program in response to changes in the child's sleep. Data pertaining to the progress of behavioural programs and the general state of the system is also stored in the memory (25).

The processing functionality of the processing unit may be provided by a custom processor design or custom software running on a general-purpose processor. Custom processors could be implemented as an ASIC or an FPGA. The processing unit may be disposed within the sensor unit (1) or the portable unit (2) or may be provided external to those units. Where the invention is implemented by custom software running on a general-purpose processor, the program for operating the system and for performing any of the methods described hereinbefore may be stored in a program memory (not shown in FIG. 7), which may be embodied as a semiconductor memory, for instance of the well-known ROM type. However, the program may be stored in any other suitable computer-readable medium (27), such as magnetic data carrier, such as a "floppy disk", CD-ROM or DVD-ROM. Alternatively as noted above, the same processing means requirement may take the form of a software service connected to a wide-area network such as the Internet.

Figure 8:
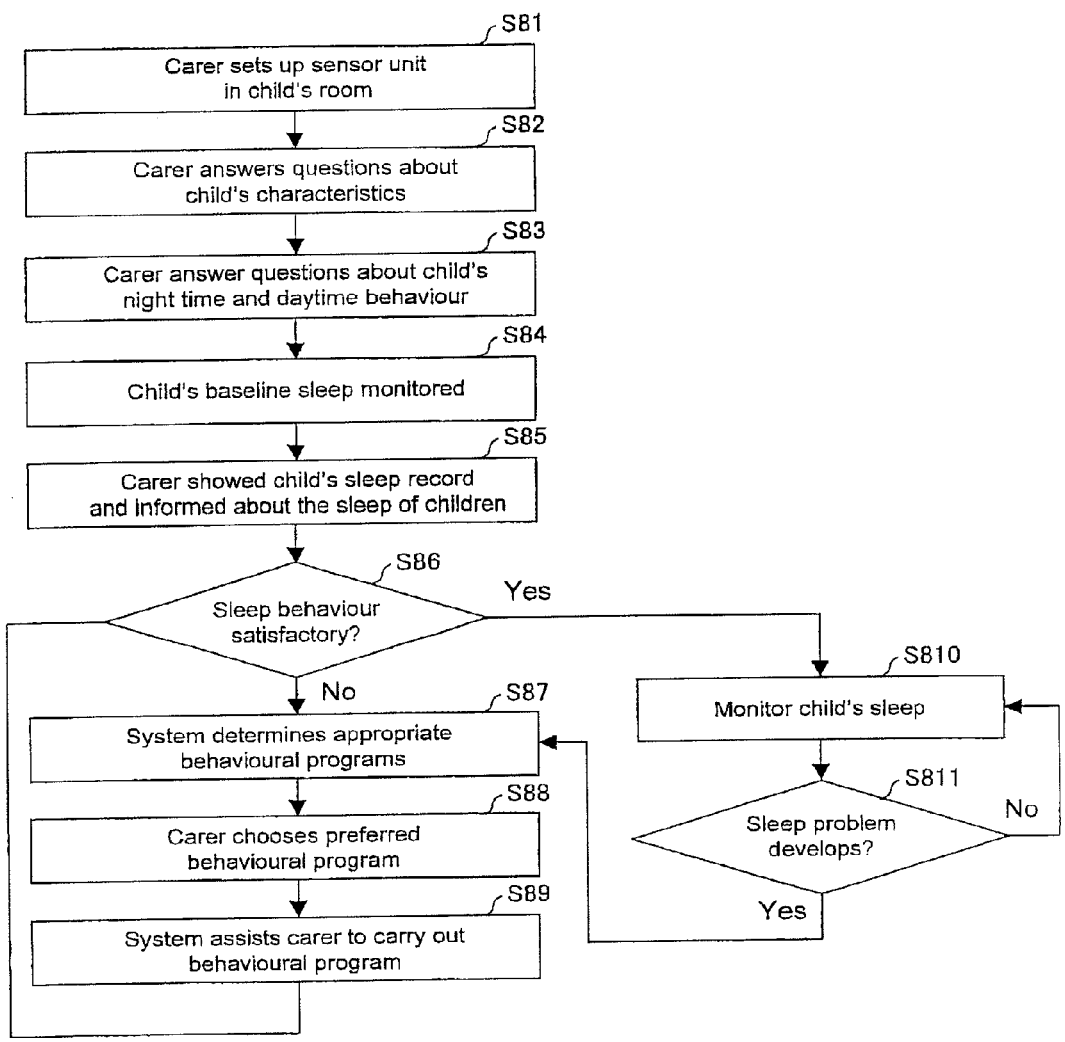
FIG. 8 shows how the system may be used.

FIG. 8 illustrates how a parent or other carer makes use of the system. The first stage (S81) is to set up the sensor unit close to where the child sleeps. This may involve placing the movement sensor sheet, film or cable in the child's bed. The portable unit provides instructions to the carer as to how to set up the sensor unit correctly. Once the unit has been placed by the carer the system checks that the sensors are operating correctly and informs the carer that set up is complete.

In the next stage, the system requests information about the child that is relevant to their sleep. This may take the form of a questionnaire. Useful information includes but is not limited to that given in Table 3. This information is required so that the child's sleep can be understood in the context of their stage of development and so that any unusual circumstances, such as chronic illness or medication use, may be taken into account by the processing unit. The carer provides the required information and answers any questions that the system asked about the child's characteristics (S82).

If the carer reports that the child suffers from an existing medical condition the system informs the carer that they should seek medical advice before carrying out any behavioural programs with the child.

TABLE 3

| Information about the child collected by the system |
| --- |
| Current medicine use |
| Date of Birth |
| Ethnicity |
| Existing medical conditions |
| Height |
| Sex |
| Temperament |
| Weight |

In a further stage, the carer answers questions about the child's typical sleep and daytime behaviour (S83). This may take the form of a questionnaire. This information is used by the processing unit to help determine the type of sleep problem that the child is experiencing if any and to identify any issues in the child's lifestyle that may be affecting their sleep. The questions used are dependent upon the age of the child. For example, for a child of 6 months the questionnaire may include questions such as 'how frequently does the child feed during the day?' and 'does the child need to be fed to fall back to sleep at night?'. For an older child the questionnaire may include 'how many caffeinated soft drinks does the child consume per day?' and 'does the child watch TV whilst in bed?'. Questions about the child's behaviour such as 'does the child suffer from behavioural problems at school?' and 'does the child have trouble concentrating for a period of 10 minutes?' are also important since these are symptoms that a carer may not obviously connect with sleep problems.

In the next stage (S84), the system records data about the child's sleep for a baseline period lasting between several days and several weeks. This baseline period allows the system to establish the child's usual sleep patterns.

Figure 9:
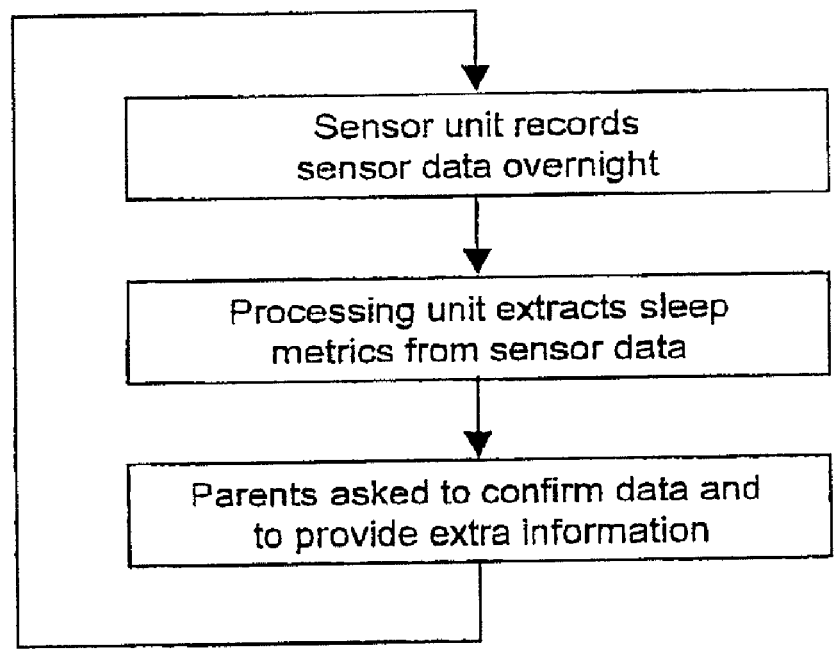
FIG. 9 shows how the system may be used during a baseline period.

FIG. 9 illustrates how the system may be used on a night to night basis during the baseline period. Firstly, the sensor unit collects data about the child's sleep overnight. This comprises movement and ambient noise data and may also include light and temperature data. Once the data is collected, the processing unit analyses the sensor data to extract a series of general sleep metrics including those given in Table 2. The sleep metrics may be calculated from data from a single sensor, or from looking for correlations between several sensors. For example, time to bed could be calculated by looking for first significant signals on the movement sensor in the evening, representing the child being physically put in the bed. However, it may be more accurate to look for early movement signals at the same time as a drop in the light signal, representing lights off. Table 4 gives examples of behavioural and environmental metrics which are calculated from the ambient noise sensor data. Table 5 gives examples of environmental metrics which are calculated from the light data. Table 6 gives examples of environmental metrics which are calculated from the temperature data.

Some time during the next day, the parent or other carer uses the portable unit to provide extra information about their child's sleep during the previous night. The information includes that given in Table 7. This extra information is stored by the processing unit with the sensor information for that night. The extra information provides a fuller picture of the child's sleep than can be derived from the sensor unit alone. It is especially important for the carer to note if the child spent part of the night out of their own bed or they napped out of their own bed, since these sleeping episodes cannot be measured by the sensor unit. The carer is also encouraged to review the sleep metrics so as to learn more about their child's sleep and has the opportunity to correct any metric that may have been misinterpreted by the sensor unit. If the carer fails to use the portable unit during the day the extra information can be added later or omitted entirely. The carer may also examine the recorded sleep metrics at any time during the baseline period.

TABLE 4

Behavioural and environmental metrics
calculated from noise sensor data

Duration of crying in bed before first sleep onset
Number, time and duration of ambient loud noises (not crying)
Number, time and duration of crying intervals after sleep onset

TABLE 5

Environmental metrics calculated from light sensor data

Dawn time
Lights off time
Lights on time
Time and duration of lights on events after sleep onset

TABLE 6

Environmental metrics calculated from temperature data

Average temperature
Time, duration and temperature reading where temperature dropped below recommended temperature for sleep
Time, duration and temperature reading where temperature increased above recommended temperature for sleep

TABLE 7

Extra information about child's sleep provided by carer

Alertness of child when put to bed
Alertness/behaviour of child during the day
Child did not sleep in normal bed last night
Child left bed and slept elsewhere for part of the night
Illness of child
Number of naps during day
Time and duration of naps during day
Time child was first put to bed
Unusual bedtime (due to family event)

The baseline period continues until the system has acquired sufficient information to give an accurate report on the child's sleep patterns or a time limit is reached. This accuracy of the sleep data may be checked by calculating the standard deviation of particular important sleep metrics and checking that they fall under a threshold. For example, if the child's average sleep onset latency is found to have a mean of 45 minutes with a low standard deviation of 5 minutes and other important sleep metrics were known similarly accurately, the baseline period would end.

When the baseline period is complete, the carer is encouraged to review and understand the sleep data acquired by the system during the baseline period (S85 in FIG. 8). The child's sleep behaviour and patterns are displayed in a clear tabular and graphical form by the portable device. The child's sleep behaviour is further compared to normal sleeping behaviour for children of similar age and development and the carer informed of the results. For example, Table 8 shows typical sleep behaviour for children of different ages. It is important that a carer has a realistic view of typical sleep patterns for children so that they do not suffer anxiety over the child's sleep simply due to their mistaken expectations.

TABLE 8

Typical sleep behaviour for children with age

| Age | Total sleep per day | Night time sleep | Naps |
|---|---|---|---|
| 0-2 months | 16-20 hours | 2-5 hours | N/A |
| 2-12 months | 12-16 hours | 9-12 hours | 1-4 per day |
| 1-3 years | 12-13 hours | 11-13 hours | 0-2 per day |
| 3-5 years | 11-12 hours | 10-12 hours | 0-1 per day |
| 6-12 years | 10-11 hours | 10-11 hours | None |
| 12-18 years | 9-10 hours | 9-10 hours | None |

The carer also has the opportunity to learn about good general sleep practices for children. These practices are often referred to as 'sleep hygiene'. The advice and recommendations provided are chosen to be appropriate to the age of the child. The advice given may include that in Table 9.

TABLE 9

Sleep advice for children of different ages

| Age | Advice |
| --- | --- |
| 0-2 months | Maintain a comfortable temperature in the room throughout the night |
| | Ensure that the baby's night time environment is distinct from the day time environment |
| 2-12 months | Put the child to bed drowsy but not asleep |
| | Avoid feeding babies older than 6 months during the night |
| 1-3 years | Establish a set bedtime routine |
| | Ensure the child does not go to sleep hungry |
| 3-5 years | Establish a set schedule of sleeping and waking times that is compatible with pre-school or kindergarten |
| | Do not change the schedule by more than 1 hour on days where there is no pre-school or kindergarten |
| 6-12 years | Avoid the presence of televisions or video games in the child's room |
| | Be sensitive to natural preferences of early rising or staying up late |
| | Ensure the child spends some time each day in sunlight |
| 12-18 years | Do not study or listen to music in bed, use it only for sleeping |
| | Avoid consuming caffeine close to bedtime |
| | Ensure regular exercise |

In the next stage (S86), the carer is asked if the child's sleeping behaviour is satisfactory, given the information that has been presented so far, or whether they would like to try to carry out a behavioural program or make a change to the child's sleep environment in order to improve the child's sleep. If the behaviour is satisfactory in the opinion of the carer, the system goes into monitoring mode. If the behaviour is not satisfactory in the opinion of the carer, the system moves to assisting the carer to choose and carry out an appropriate behavioural program or environmental change.

In this case (S87 in FIG. 8), the processing unit uses algorithms to analyse the sleep metrics and environmental data recorded during the baseline monitoring period to identify which behavioural programs or environmental changes would benefit the child. The system takes into account the child's age and other characteristics to ensure that its recommendations are appropriate to the particular child.

The processing unit chooses and recommends behavioural programs including those in Table 10. For example, if the sleep metrics indicate that the child spends a long time restless in bed before sleep (a long sleep onset latency) then a program of bedtime resetting would be appropriate, where the child's bedtime is initially set later and subsequently moved earlier. On the other hand, if a young child wakes frequently during the night (high number and length of nocturnal awakenings) and cries until they are comforted (high number of crying intervals after sleep onset), then a program of extinction that limits parental contact would be appropriate. In most circumstances several behavioural programs will be appropriate. Furthermore, some behavioural programs can be carried out simultaneously, for example a graduated extinction program with the carer additionally using positive routines.

If the processing unit identifies an environmental change that would benefit the child's sleep it is also recommended to the carer. The system identifies environmental factors by comparing environmental data recorded during the baseline period to established norms or by correlating environmental data with other sleep metrics. For example, if the temperature in the room is found to drop below recommended levels for significant parts of the night, the system will recommend increasing the temperature by using a heater. Other recommendations are based on correlations between different sensor data. For example, if the child is typically found to wake at a certain time from the movement data and that time corresponds to the onset of dawn as calculated from the light data, the system will alert the carer to the fact that the child may be being woken by bright light. In this case the system may recommend heavier curtains for the child's room.

TABLE 10

Behavioural programs

| Program | Description |
| --- | --- |
| Custom program | Carer carries out change of their own design and system monitors effect |
| Dissociating feeding from sleep-wake transitions | Time between feeding increased during the day and feeding progressively faded out at night |
| Extinction | Child's cries are ignored until child sleeps |
| Graduated extinction | Child's cries are ignored for progressively longer times |
| Graduated extinction with presence | Child's cries are ignored for progressively longer times but parent or carer stays with child |
| Positive routines | Child taught to associate bedtime with sleep through quiet activities in the evening |
| Reset bedtimes | Child's bedtime is set to be in line with current sleep time and then moved earlier |
| Reset bedtimes with response cost | Child's bedtime is set to be in line with current sleep time and then moved earlier. If child does not sleep they are removed from bed. |
| Scheduled awakenings | Child woken before typical awakening times |

The carer is presented with a choice of suitable behavioural programs and environmental changes that are recommended for the child.

Information about each of the behavioural changes is given to the carer so that they can fully understand what is involved. Since the carer will be carrying out the behavioural program it is important that they have the option to choose a program they prefer (S88). For example, although extinction is an effective technique some carers find leaving the child to cry by themselves all night unacceptable. Such carers may prefer a technique of graduated extinction with parental presence where they remain with their child whilst they cry but limit direct interaction.

For any recommended environmental changes, the carer may wish to make environmental changes and then monitor the child to see if the changes have improved the child's sleep. In this case a 'custom program' option is used where the child's sleep is monitored and analysed for improvements. Alternatively, the carer may wish to make the environmental changes immediately and also carry out a behavioural program. In this case a behavioural program is chosen and proceeds as normal.

The carer also has the option to carry out their own changes to the child's sleep behaviour or environment and use the system to monitor the results. This may be based on the advice on children's sleep behaviour given to the carer. In this case a 'custom program' option is used where the child's sleep is monitored and analysed for improvements.

Figure 10:
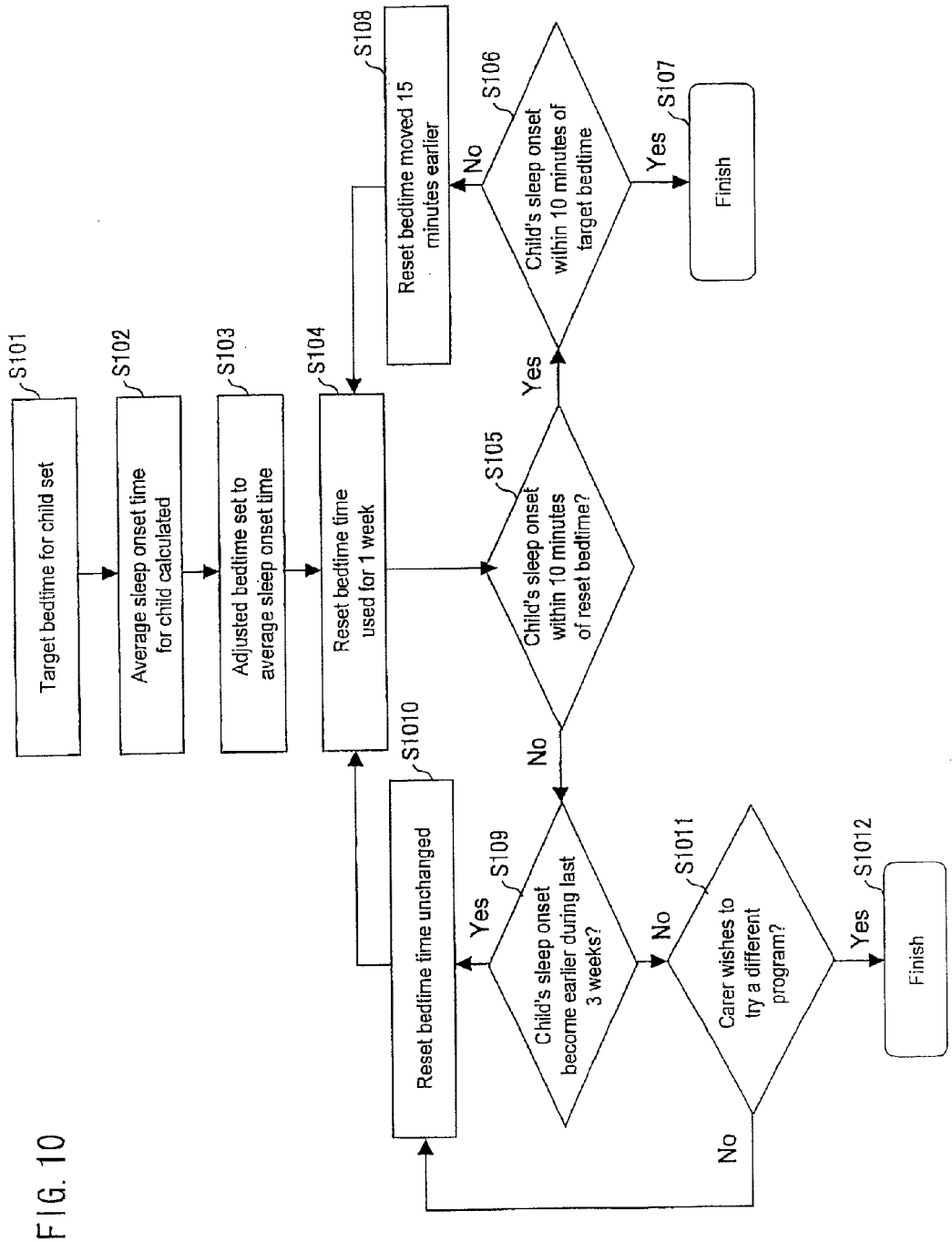
FIG. 10 shows how a behavioural program of reset bedtimes may be implemented by the system.

Once a behavioural program is chosen, the system assists the carer to carry out the program (S89). FIG. 10 shows how the system assists the carer to carry out a typical behavioural program of reset bedtimes.

Reset bedtimes is a behavioural program designed to help children who either spend a long time in bed without sleeping or strongly resist going to sleep at the time desired by the carer.

At the first stage, the carer is requested to set a target for the child's sleep. In a program of reset bedtimes, the carer chooses (S101) a desired bedtime for the child that is suitable for the child's age and fits with the carer's lifestyle. The system suggests suitable times based on typical data for children of similar ages, for example from that given in Table 8. The target for the behavioural program is then set by the processing unit to be that the child goes to bed at the desired time and sleeps within 10 minutes.

Once a suitable target has been set, the system designs a personal behavioural program for the particular child. The personal behavioural program is based on the sleep metrics recorded during the baseline monitoring period. The system has in its memory the sleep onset times for the child during the baseline monitoring period. At stage 2 (S102 in FIG. 10), the average (mean) sleep onset time for the child during the baseline period is calculated, excluding any times when the carer recorded that the child was ill or the bedtime was unusual. At stage S103 the first reset bedtime for the child is then set to the average sleep onset time recorded. For example, if the child's average sleep onset time was recorded by the sensor unit as 21:10 hrs then the reset bedtime for the child would be set to 21:10 hrs. In stage S104, the carer is instructed to use the reset bedtime for a period of one week. The child is expected to be very sleepy and ready to go to bed at this time.

Figure 11:
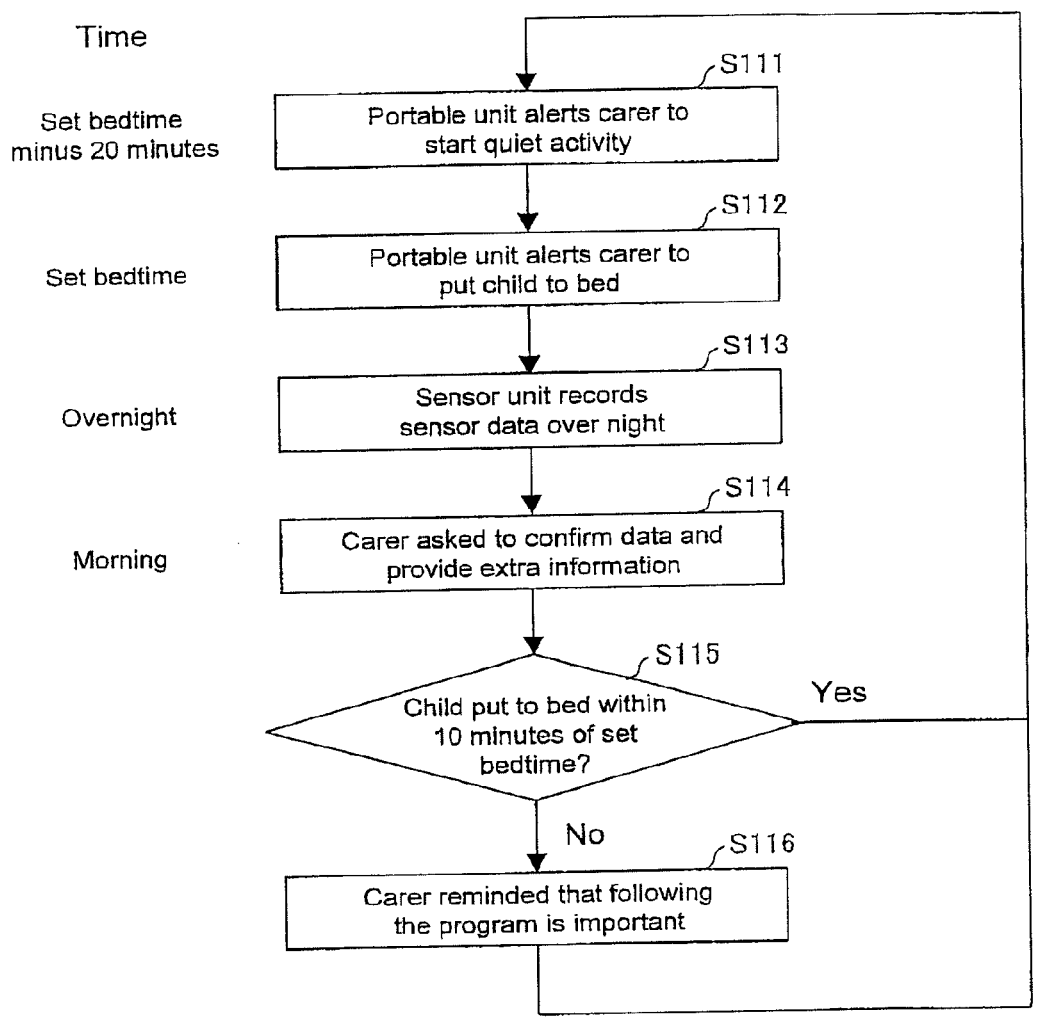
FIG. 11 shows how a behavioural program of reset bedtimes may be implemented on a nightly basis by the system.

FIG. 11 shows how the system is used on a night-by-night basis during the behavioural program of reset bedtimes. At stage S111, 20 minutes before the reset bedtime, the portable unit alerts the carer and instructs the carer to spend the next 20 minutes doing a quiet activity with the child such as reading a bedtime story, having a bath or brushing teeth and preparing for bed. An alert can take the form of an audio signal, a vibration or a message on the display. Typically an alert may be initially in the form of a message and, if the carer does not respond during a set time period, an audio or vibration alarm may be used. This is so as not to disturb a tired child unnecessarily. At stage S112, the portable unit alerts the carer that it is time to stop the quiet activity and put the child to bed.

The child's sleep continues to be tracked overnight by the sensor unit (stage S113). During the next day (stage S114), the carer is encouraged to continue to enter extra information about the child's sleep into the portable unit. This information includes that in Table 7. This information both assists the algorithm in identifying non-typical nights that should not be included in analysis and also helps to keep the carer involved with the progress of the program. The carer is encouraged to enter information at an appropriate time. For example, the carer can time the child's naps during the day by pressing a button or similar on the portable unit when the child sleeps and wakes.

The system also checks that the carer put the child to bed within 10 minutes of the reset bedtime at stage S115. The time the child is put to bed is found from the calculated sleep metrics from the sensor data. If the child was not put to bed within 10 minutes of the reset bedtime, and there was no unusual circumstance recorded by the carer, then the carer will be reminded about the importance of following the program closely (stage S116).

If the carer records an unusually high number of non-typical nights, for example more than 2 per week, the system will alert the carer to this fact and remind the carer that the behavioural program will not be effective or will take much longer if the child is not kept to a strict sleep regimen.

After the behavioural program has been used for one week (S105 in FIG. 10), the child's average sleep onset time for this week (excluding nights marked as unusual) is compared with the current reset bedtime. If the child's average sleep onset time is within 10 minutes of the current reset bedtime, it is further checked (S106) to see if it is within 10 minutes of the target bedtime. If this is true then the behavioural program has completed successfully (S107) and is over. The system then enters monitoring mode. If the child's sleep onset is not yet within 10 minutes of the target bedtime, then the reset bedtime is moved 15 minutes earlier for the next week (S108). The program then continues from S104 using the reset bedtime as revised.

If the child's average sleep onset time is not within 10 minutes of the current reset bedtime, the child's average sleep onset time is further checked to see if it has become earlier during the previous 3 consecutive weeks (S109). If the child's sleep onset time has become earlier within the last 3 weeks, then the child is responding to the program slowly and the program continues as normal. In this case the reset bedtime for the following week is unchanged (S1010). However, if the child's sleep onset time has not become earlier during the previous 3 weeks, it is possible that this behavioural program is no longer effective for the particular child. In this case, the carer is informed of the situation and is asked if they wish to continue with the program or if they wish to choose another program that may be more effective for the child (S1011). If the carer wishes to continue with this program then the reset bedtime is unchanged (S1010) and the program continues. However, if the parent wishes to end the behavioural program, the routine concludes (S1012) and the system returns to S87 in FIG. 8, The carer is informed about the progress of the program throughout its duration via the portable unit. The carer can check the child's bedtimes and sleep onset times and receives encouragement and advice whenever the system is used. For example, if the child's sleep onset time does not get earlier at S105 as in FIG. 10, the carer may be reminded that the program often takes a period of several months to complete and an improvement cannot be expected every week. The carer is told that if they continue adhering to the program, it is highly likely that the child's sleep behaviour will improve.

As described above, if the carer does not put the child to bed within 10 minutes of the reset bedtime, the carer is reminded of the importance of complying with the program (S116 in FIG. 11). However, if the carer persists in failing to put the child to bed at the appropriate time the system can move the reset bedtime of the child earlier or later to help the carer comply. Having the carer comply with a modified program will be more beneficial for the child than having the carer fail to comply with the program altogether. The system will then continue on the routine in FIG. 10 using the adjusted bedtime.

Figure 12:
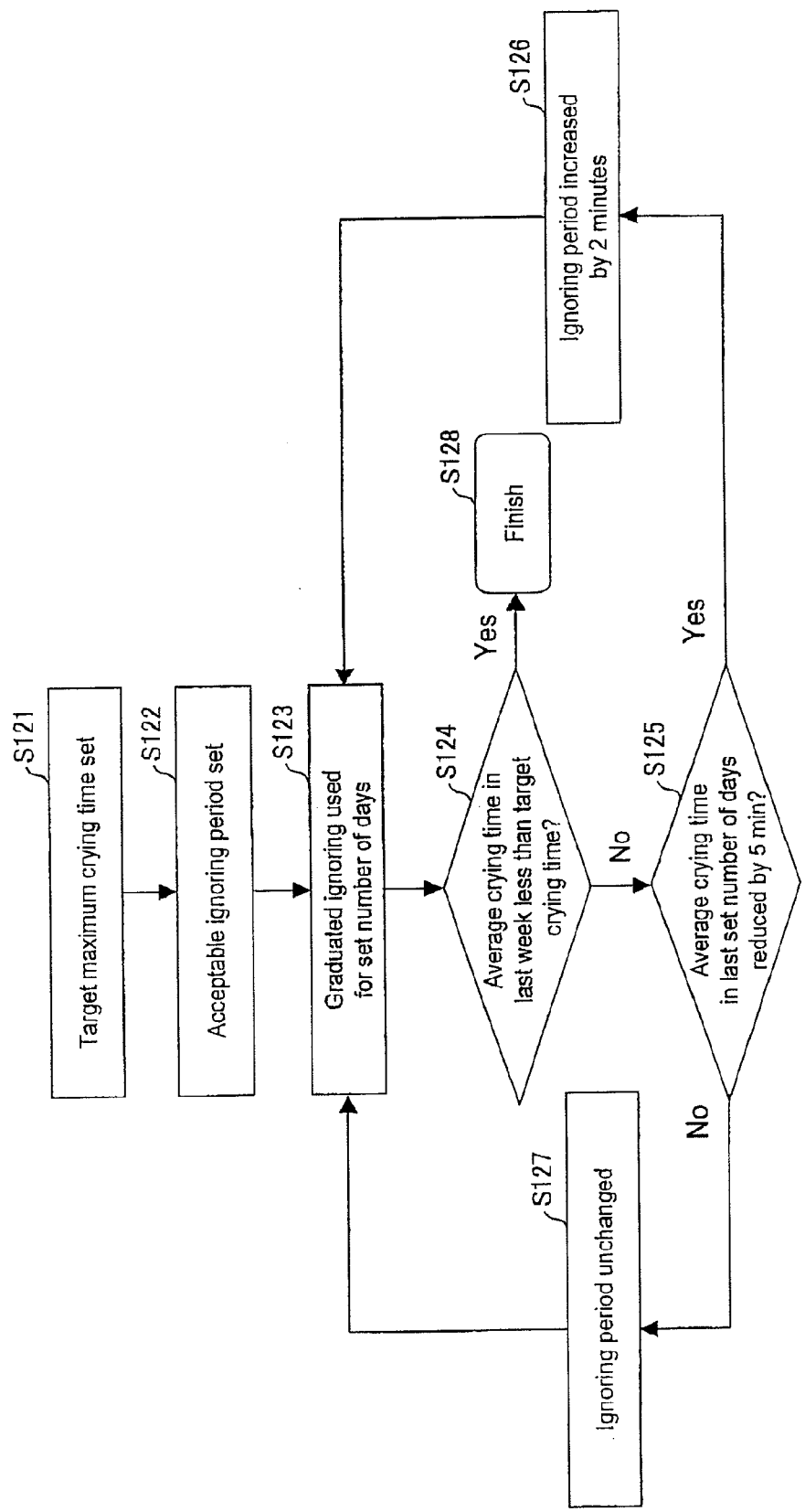
FIG. 12 shows how a behavioural program of graduated extinction may be implemented by the system.

FIG. 12 shows how the system assists a carer to carry out a different behavioural program of graduated extinction.

Graduated extinction is a behavioural program suitable for children who have difficulty going to sleep without being comforted by a carer. Both at bedtime and after any awakenings during the night the child will cry until they are comforted by a carer. Graduated extinction teaches the child to sleep without the involvement of the carer by progressively limiting the time the carer spends comforting the child.

In stage S121, the carer sets a maximum acceptable time for the child to cry before they sleep based on personal tolerance and a recommendation provided by the system based on the average behaviour of children with similar characteristics. A typical recommendation would be 5 minutes and the behavioural program will end when the child reaches this point.

In order to carry out a program of graduated extinction, the child's cries must be ignored for a length of time, However, the carer may not wish to ignore the child for too long. Therefore the system recommends an initial program of ignoring periods and the carer confirms that this is acceptable to them (S122). If not, a program of shorter ignoring periods is agreed with the carer. Whilst using a program of shorter periods may require a longer program duration to be effective, it is most important that the carer is able to adhere strictly to the program.

Figure 13:
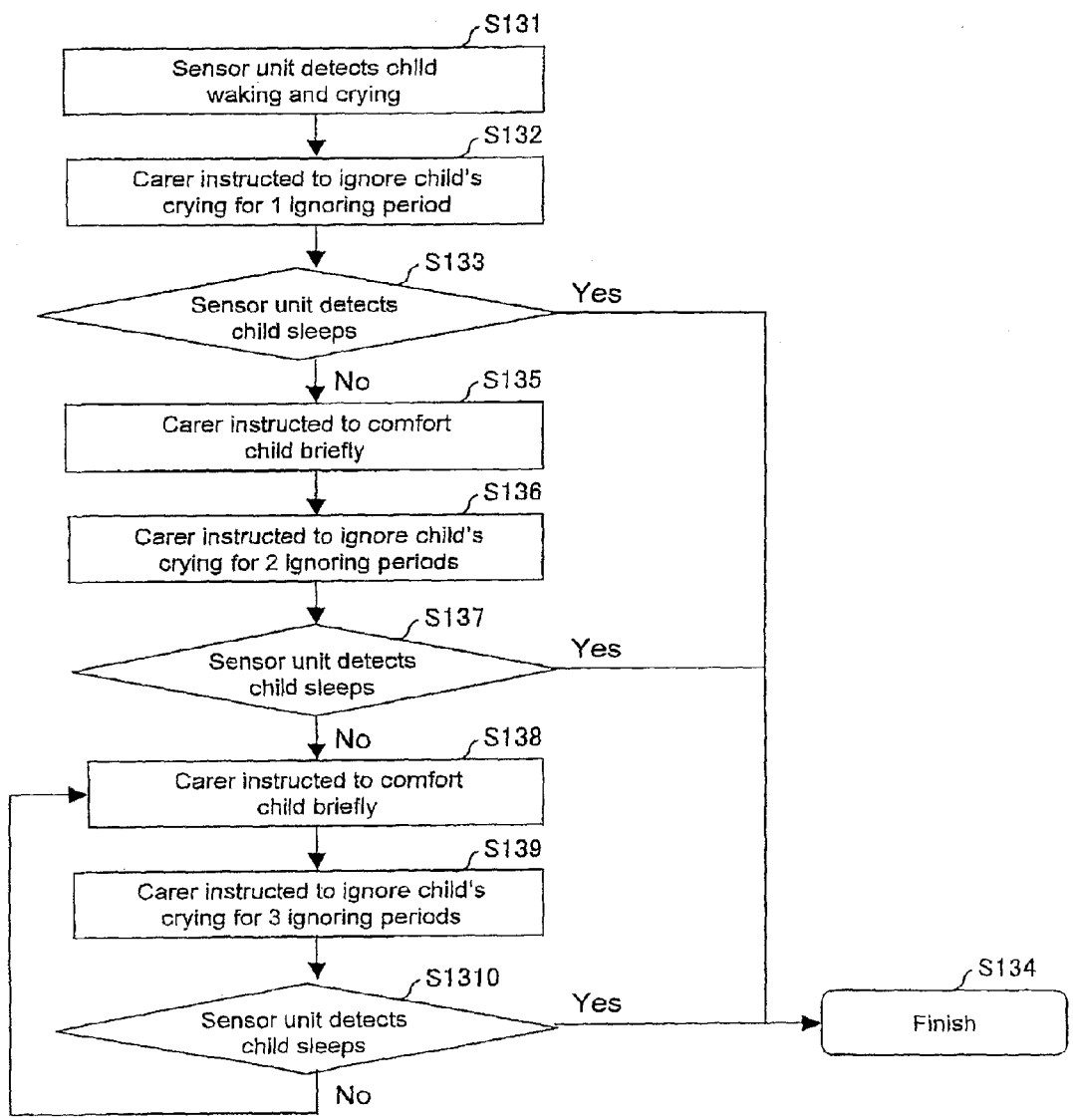
FIG. 13 shows how a behavioural program of graduated extinction may be implemented on a nightly basis by the system.

In stage S123, the graduated extinction scheme is used for a set number of days, typically two, before reassessing the length of the periods. FIG. 13 shows how the system assists the parents carrying out the graduated extinction program. The routine in FIG. 13 is carried out if the child cries when they are put to bed or whenever they cry after waking during the night. The routine starts (S131) when the sensor unit detects the child waking and crying. The portable unit alerts the carer and instructs them at stage S132 to ignore the child's crying for a single multiple of the currently set ignoring period. For example, if the ignoring period was 5 minutes, the carer would be instructed at stage S132 to ignore the child for 5 minutes. The ignoring time remaining may be displayed to the carer as a countdown on the portable device. During the ignoring period, the sensor unit continues to record the ambient noise by the child. If the sensor unit detects that the child has ceased crying during this period (stage S133) this indicates that the child may have fallen asleep and the routine ends (S134). If not, at the end of the ignoring period, the portable unit alerts the carer and instructs them to comfort the child briefly (S135), typically for not more than 1 minute. At the end of the 1 minute comforting period the portable unit will alert the carer and instruct them to cease comforting the child.

The carer is then instructed (S136) to ignore the child for a longer period of time, typically twice the set ignoring period. For example, if the ignoring period was 5 minutes, the carer would be instructed to ignore the child for 10 minutes. If the sensor unit detects that the child sleeps during this period at S137, the routine ends; if not the carer is instructed to comfort the child for a short period of time (S138). The carer is then instructed (S139) to ignore the child for a longer period of time, typically three times the set ignoring period. If the sensor unit detects that the child sleeps during this period (S1310), the routine ends. If not, the routine returns to S138 and the carer is instructed to comfort the child for a short period of time. The carer is then (S139) instructed to ignore the child as before for three times the set period. The routine continues in this fashion until the child sleeps.

It may be that the carer cannot bear to ignore the child for as long as requested by the portable unit. In this case, the carer can inform the portable unit via a button press or other method that they are comforting the child before the scheduled time. This may also be detected automatically by the sensor unit, for example by noting that the child is being lifted from the bed. If the carer comforts the child early, the portable unit reminds the carer that the program can only be effective if the carer obeys it rigorously. If the carer persists in comforting the child early, the system can alter the routine to shorten the ignoring periods to a length the carer finds acceptable. The ignoring periods for the next night will then be set to this shorter period of time.

Referring to stage S123 of FIG. 12, after graduated extinction has been used for the set number of days, the system uses the data from the sensor unit to calculate an average crying time for the child during the last week. If the average crying time is found at stage S124 to be less than the target maximum crying time, the program ends (S128). If not, the routine continues to stage S125. Calculation stage S124 is not used until a week of data has been collected.

At stage S125, the average crying time for the last set number of days is compared to that of the preceding set number of days. If the average crying time has reduced by 5 minutes the ignoring period is increased by 2 minutes (S126). If not, the ignoring period is left unchanged (S127). The first time, there is no relevant preceding data and the system must proceed via S127. In any case the system returns to S123 and graduated extinction is used for another set number of days and the child's crying time is reassessed as in FIG. 12.

Graduated extinction can be a difficult behavioural program for a carer to carry out since it can be hard to ignore a child's crying. Furthermore, it is known that in an extinction program the child's behaviour may worsen for a few days before improving. If the system detects that the child's crying time is unchanged or has increased, the portable unit will inform the parents that this is normal behaviour and provide encouragement that if they continue with the program they will see good results.

During any behavioural program, if the child does not respond to the program for a long period of time or if the carer wishes, the program may be ended prematurely. The carer may then choose a different behavioural program or place the system into monitoring mode.

When a behavioural program ends successfully, the system returns to S86 in FIG. 8 and the carer is asked if the child's sleeping behaviour is now satisfactory. If the child's behaviour is satisfactory and the carer does not wish to continue with a behavioural program, the system goes into monitoring mode (S810). If the carer wishes to try another behavioural program, change the child's target bedtime or other behaviour or to continue carrying out a behavioural program indefinitely, then the system returns to S87 in FIG. 8 and then assists the carer in carrying out the behavioural program. Furthermore, when in monitoring mode, the carer can always choose to carry out a behavioural program, in which case the system returns to S87 in FIG. 8 and assists the carer in doing this.

In monitoring mode, the system continues to collect sensor data on the child's sleep each night. As for the baseline period (FIG. 9) the system continues to calculate sleep metrics and the carer is able to provide additional information about the child's sleep. It is likely that in the monitoring period the carer will provide less information. At any time during the monitoring period the carer can review the child's current sleep behaviour on the portable unit which is presented in an easy to understand fashion.

In the monitoring mode, the system uses algorithms to look for changes in the child's sleep behaviour that may lead to decreasing quality of sleep and therefore could be addressed using a behavioural program. Changes in children's sleep behaviour can be caused by changes in their life, for example a baby starting to eat solid food or an older child starting school. The carer can provide information about such changes with the portable device which can help the processing unit to recommend appropriate behavioural programs. The sleep behaviour of children also changes as they age. Therefore the processing unit compares changes in sleep behaviour to typical changes expected for children of the age of the child. If the change is typical, the portable unit informs the carer of this and suggests that a behaviour program is not necessary in this case.

Any negative changes in sleep behaviour must be sustained over a long period of time of typically at least two weeks before the system will alert the parents and recommend a behavioural therapy. This avoids any transient changes or changes due to short illnesses causing the system to alert the carer.

Typical examples of negative changes in sleep behaviour include those listed in Table 11. If a sustained negative change is found to occur at step S811 (FIG. 8), the carer is alerted. The system then moves to stage S87 as shown in FIG. 8 and suggests suitable behavioural programs for the child based on the recent changes in sleep behaviour.

TABLE 11

Negative changes in sleep behaviour

Being unable to rise in the morning
Increased crying before bed or during the night
Increased number or duration of awakenings during the night
Increased sleep onset latency
Waking very early and being unable to resume sleep The three components of the system, the sensor unit (1), the processing unit (3) and portable unit (2) all contain network connections so as to be able to communicate with each other. If the processing unit is disposed within either the sensor unit or the portable unit it is possible that both units will share the same network connection.

The network connecting the units is preferably wireless so that the portable unit can be easily carried by the carer without the necessity of a wired connection. A wired network connection may be possible for the sensor unit or processing unit.

Preferably each component is connected via its network connection to a wide-area network such as the Internet. In this way the portable unit may be taken with the carer anywhere within or outside of the house and still be used to interact with the system. Furthermore this allows the carer to continue a behavioural program even if the child is away from its normal bed, for example staying with relatives or on a short holiday. The portable unit continues to instruct the carer as to the appropriate bedtime for the child, how to time parental contact or to continue other instructions as appropriate for the current behavioural program. In this case the sensor unit may not be able to record data on the child's sleep and in this case the carer should report that the child was not in its usual bed using the portable unit as normal. If the carer feels confident in doing so, they may also report the child's sleep behaviour via the portable unit and this information will be sent to the processing unit and used to continue to track the progress of the behavioural program.

In the case where each unit communicates with the other units via a wide area network such as the Internet, the processing unit may take the form of software service which is located outside of the home where the system is being used. In this case the processing unit software may be deployed on a single server computer, server cluster or as a cloud computer service. In this fashion a software service with the function of a plurality of processing units may be deployed. The software service will store and process the data from a plurality of portable and sensor units used to monitor a plurality of children. However, the functionality of the system as experienced by the carer or child is not changed in any way in this case.

Use of the software service as described may require the payment of a subscription or fee by the parent or carer. Furthermore, additional services may be offered to the parent or carer for free or for an additional fee. Since the processing unit stores a large amount of sleep data for the child, it is possible that a sleep specialist or doctor can monitor the sensor data for the child and advise the carer on how to use the system most effectively. For example, the sleep specialist could advise choosing a particular behavioural strategy and setting the parameters such that they will be particularly effective for the child. The sleep specialist could then continue to review the child's progress and adjust the behavioural program appropriately. Other services that may be offered to the carer include purchasing products connected with baby care, providing discussion forums to discuss children with other carers and informative audio or video lectures.

In the case where each unit communicates with the other units via a wide area network such as the Internet, other devices which are also connected to the wide area network may be used by the user to interact with the system. For example, a laptop computer, desktop computer or mobile phone may be used to access the child's sleep history, access information about the behaviour programs or perform other functions of the portable unit. This may be achieved by providing a web interface at the processing unit which may be accessed by any web-enabled device.

Networking technologies suitable for connecting the units to a wide area network such as the Internet include WiFi (802.11), GSM, GPRS and 3G. Wired network technologies, which may be appropriate for the sensor unit or for an external server hosting the processing unit as a software service, include Ethernet. Point-to-point network technologies including Bluetooth, ZigBee and Wireless USB may also be used to network the units. If the portable unit does not have an independent means of connecting to the Internet it cannot be used outside of the house. If no component has a means of connecting to the Internet then the System is self-contained in the carer's house.

Embodiment 2

In embodiment 2 a system is provided as in embodiment 1 where the system is additionally able to provide a printed or electronic record of the child's sleep data and the actions taken by the carer. The format of the data is such as to provide a clear picture of the child's sleep problems. Such a record can be taken to a sleep specialist or doctor who can use the data to understand the child's sleep problems and treat the child as appropriate.

The treatment may take the form of advising the carer how to use the functions of the system, for example to carry out a behavioural program that the specialist believes is most suitable for the child. The treatment may however not involve using the behavioural program functions of the system.

The system may be placed in monitoring mode during the course of the treatment by the specialist and further printed or electronic records produced as the treatment progresses. In this way the specialist can monitor the effect of the treatment on the child's sleep behaviour.

Embodiment 3

In embodiment 3 a system is provided as in embodiment 1 where it is adapted for use for training animals and household pets, in particular young dogs. In this embodiment the sensor unit is deployed where the animal typically sleeps, for example a dog basket or kennel. Furthermore, the system is pre-loaded with information on typical sleep patterns for animals, for example dogs of particular ages and breeds. The algorithms are adapted such as to identify sleep problems in animals that may be eliminated by known animal training methodologies.

In the embodiments of the present invention, an "objective parameter" is meant a parameter that may be measured objectively by a sensor, and that does not require any subjective judgement by a user.

In some embodiments, the carer is able to improve the sleep behaviour of the human or animal in their care by acting upon the recommendation(s) for behavioural programs and/or for actions for implementation. The recommendations may potentially relate to any factor that influences the sleep behaviour of the human or animal, including (for example, and without limitation), the temperature in a bedroom, the time at which a child is put to bed and/or is woken up, eating patterns or times, exercise patterns and times, times and patterns of contact between the child and the carer etc. The recommendations may be modified over time, as the processor detects changes in the sleep behaviour of the human or animal, and/or on the basis of information supplied by the carer via the portable user interaction device.

The at least one sensor may not include any sensor attached to the human or animal.

The method may be applied to improve the sleep behaviour of a baby, infant or child. Alternatively it may be applied to an adult in the care of the carer due to old age or mental or physical disability. Alternatively it may be applied to a pet animal in the care of the carer.

The method may comprise monitoring, using a plurality of sensors, both physiological and environmental parameters non-obtrusively such that they do not affect the sleep of the user.

The physiological and environmental parameters monitored may include movement and one or more of temperature, ambient noise, light and humidity.

A movement sensor may be employed which comprises a piezoelectric sheet, cable or film disposed below the human or animal in bed and connected to the sensor unit via a cable or wireless connection.

A sensor reading or multiple of sensor readings from the or each sensor may be stored with a time code in a second memory, and sensor data stored in the second memory may be sent periodically, or on request, to the processing means.

The method may comprise sampling data from the or each sensor at a frequency 0.1 Hz to 100 Hz before storage to the second memory.

The portable user interaction device may be a mobile phone.

The method may further comprise the portable user interaction device prompting the carer to carry out actions required to implement a behavioural program recommended by the processing means.

The processing means may be separate from the portable user interaction device.

The processing means may take the form of a software service connected to a wide-area network, for example the Internet.

The processing means may monitor compliance with any behavioural program or action presented to and chosen by the carer and provides (i) one or more of warnings, guidance, advice and message(s) of encouragement to the carer to aid compliance with any chosen program or action and/or (ii) one or more updated recommendations for behavioural programs and/or actions.

The processing means may generate an alert to the carer via the portable user interaction device after a pre-defined number of nights of lack of improvement in sleep behaviour.

The processing means may generate an alert to the carer via the portable user interaction device after a pre-defined number of nights of a worsening in sleep behaviour.

The first memory may store instructions for both behavioural programs and actions for altering one or more environmental parameters.

The method may further comprise the carer setting, via the portable user interaction device, a customized program.

The carer may input, to the portable user interaction device, information on choice and implementation of a recommended behavioural program or action, and wherein the input information is sent to the processing means for correlation with data received from one or more of the at least one sensor.

Prior to recommendation of any behavioural program or action, the processing means may receive data from the at least one sensor for a period, whereby a baseline for data received from the or each sensor and/or a baseline sleep metric is established.

The processing means may be present in either of the sensor unit or portable device or separate therefrom. It may preferably take the form of hardware and/or software, e.g. preferably a software service accessible via a wide-area network such as the Internet. It will be recognized that in this case, a combination of hardware units will be provided to the carer comprising elements (i), (ii) and (iv) of the system.

Recommendations made by the processing means will generally be with the aim of improving the sleep behaviour of the human or animal, but can include monitoring only if the information provided to the processing means is correlated with the lack of a significant sleep problem requiring rectification. In such circumstances, the processing means may generate an alert to the carer via the portable user interaction device after a pre-defined number of nights of a worsening in sleep behaviour.

Such a system may, for example, be advantageously employed by a parent or other carer to modify sleep behaviour of a baby, infant or child. It may be adapted for a specific age range, e.g. babies and infants of less than 2 years and for older children. While such a system is envisaged as particularly useful for use by parents in improving sleep of young children, additionally or alternatively a system of the invention may be adapted for use by a carer looking after an adult, e.g. due to old age or mental or physical disability. A system of the invention may also be adapted for use with animals and may, for example, be advantageous to pet owners seeking to improve sleep of domestic pets, especially dogs.

It will be recognized that in use a system of the invention may recognize a sleep problem requiring specialist, even medical treatment, in which case a recommendation will be provided to seek specialist advice, e.g. from a doctor. However, it will be appreciated that the portable user interaction device element of the system can only impart information to the carer and encourage behavioural action, which might include seeking medical treatment for an underlying medical problem affecting sleep, but cannot provide treatment per se.

Preferably the one or more sensors do not include any sensor attached to the human or animal.

The system may comprise a plurality of sensors adapted to monitor both physiological and environmental parameters non-obtrusively such that they do not affect the sleep of the user.

The physiological and environmental parameters monitored may include movement and one or more of temperature, ambient noise, light and humidity.

A movement sensor may be employed which comprises a piezoelectric sheet, cable or film disposed below the human or animal in bed and connected to the sensor unit via a cable or wireless connection.

The sensor unit may contain a second memory and a real time clock whereby each sensor reading or multiple of sensor readings from each sensor for storing in the memory is stored with a time code, and sensor data stored in the second memory is sent periodically, or on request, to the processing means.

Within the sensor unit signal data from the or each sensor may be sampled by a processor at a frequency of 0.1 Hz to 100 Hz before storage to the second memory.

The portable user interaction device may be a mobile phone.

The portable user interaction device may also have an alerting means for prompting the carer to carry out actions required to implement a behavioural program recommended by the processing means.

The processing means may be separate from the sensor unit and the portable user interaction device.

The processing means may take the form of a software service connected to a wide-area network.

The processing means may monitor compliance with any behavioural program or action presented to and chosen by the carer and provides (i) one or more of warnings, guidance, advice and message(s) of encouragement to the carer to aid compliance with any chosen program or action and/or (ii) one or more updated recommendations for behavioural programs and/or actions.

The processing means may generate an alert to the carer via the portable user interaction device after a pre-defined number of nights of lack of improvement in sleep behaviour, or after a pre-defined number of nights of a worsening in sleep behaviour.

The first memory may store instructions for both behavioural programs and actions for altering one or more environmental parameters.

The carer may be able to set via the portable user interaction device a customized program.

A sleep management system of the second aspect of the invention may be implemented as a combination of hardware units, which hardware units comprises (i) the required sensor(s) (ii) the sensor unit and (iii) the portable user interaction device. Alternatively, one or more of the components may be integrated with one another—for example, the sensor(s) may be integrated with the sensor unit.

According to a third aspect of the invention, there is provided a method of improving the sleep behaviour of a human or animal in the care of a carer which comprises use by the carer of a system of the second aspect.

According to a fifth aspect of the invention there is provided a computer-readable medium containing instructions that, when executed by a processor, cause the processor to perform a method of the first or fourth aspect.

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

The invention claimed is:

1. A method for use by a carer of a human or animal different from the carer to improve the sleep behaviour of the human or animal under care, the method comprising:
   (i) monitoring, using at least one sensor, one or more objective parameters relevant to sleep-related behaviour of said human or animal, said parameters being selected from physiological parameters and environmental parameters and including at least movement of the human or animal and/or electrical signals indicative of brain activity of the human or animal after having been put to bed;
   (ii) communicating data from said at least one sensor to a processing means;
   (iii) at said processing means, using said data in selecting from a first memory one or more recommendations for behavioural programs to improve the sleep behaviour of the human or animal and/or actions for implementation by the carer to improve the sleep behaviour of the human or animal; and
   (iv) sending said one or more recommendations from said processing means to a portable user interaction device for presenting the recommendation(s) to the carer via a display, said portable user interaction device also enabling the carer to input information which is fed back to said processing means;
   wherein said processing means updates the one or more recommendations sent to said portable user interaction device on the basis of changes in detected sleep behaviour of said human or animal and/or on the basis of information input to said portable user interaction device, and
   wherein said processing means generates an alert to the carer via said portable user interaction device after a pre-defined number of nights of lack of improvement in sleep behaviour.

2. A method for use by a carer of a human or animal different from the carer to improve the sleep behaviour of the human or animal under care, the method comprising:
   (i) monitoring, using at least one sensor, one or more objective parameters relevant to sleep-related behaviour of said human or animal, said parameters being selected from physiological parameters and environmental parameters and including at least movement of the human or animal and/or electrical signals indicative of brain activity of the human or animal after having been put to bed;
   (ii) communicating data from said at least one sensor to a processing means;
   (iii) at said processing means, using said data in selecting from a first memory one or more recommendations for behavioural programs to improve the sleep behaviour of the human or animal and/or actions for implementation by the carer to improve the sleep behaviour of the human or animal; and
   (iv) sending said one or more recommendations from said processing means to a portable user interaction device for presenting the recommendation(s) to the carer via a display, said portable user interaction device also enabling the carer to input information which is fed back to said processing means;
   wherein said processing means updates the one or more recommendations sent to said portable user interaction device on the basis of changes in detected sleep behaviour of said human or animal and/or on the basis of information input to said portable user interaction device, and
   wherein said processing means generates an alert to the carer via said portable user interaction device after a pre-defined number of nights of a worsening in sleep behaviour.

* * * * *